(12) United States Patent
Deihimi et al.

(10) Patent No.: US 12,098,428 B2
(45) Date of Patent: Sep. 24, 2024

(54) FREQUENT EGFR AND NTRK SOMATIC MUTATIONS IN COLORECTAL CANCER (CRC) WITH MICROSATELLITE INSTABILITY (MSI)

(71) Applicant: Institute For Cancer Research, Philadelphia, PA (US)

(72) Inventors: Safoora Deihimi, Philadelphia, PA (US); Michael Slifker, Philadelphia, PA (US); Wafik S. El-Deiry, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 812 days.

(21) Appl. No.: 16/487,272

(22) PCT Filed: Feb. 26, 2018

(86) PCT No.: PCT/US2018/019661
§ 371 (c)(1),
(2) Date: Aug. 20, 2019

(87) PCT Pub. No.: WO2018/157032
PCT Pub. Date: Aug. 30, 2018

(65) Prior Publication Data
US 2021/0054463 A1 Feb. 25, 2021

Related U.S. Application Data

(60) Provisional application No. 62/463,664, filed on Feb. 26, 2017.

(51) Int. Cl.
| | | |
|---|---|---|
| *C12Q 1/6886* | (2018.01) | |
| *A61K 31/506* | (2006.01) | |
| *A61K 31/517* | (2006.01) | |
| *A61K 31/5377* | (2006.01) | |
| *A61P 35/00* | (2006.01) | |
| *C07K 16/22* | (2006.01) | |

(52) U.S. Cl.
CPC .......... *C12Q 1/6886* (2013.01); *A61K 31/506* (2013.01); *A61K 31/517* (2013.01); *A61K 31/5377* (2013.01); *A61P 35/00* (2018.01); *C07K 16/22* (2013.01); *C12Q 2600/112* (2013.01); *C12Q 2600/156* (2013.01)

(58) Field of Classification Search
CPC .. C12Q 1/6886; A61K 31/506; A61K 31/517; C07K 16/22
See application file for complete search history.

(56) References Cited

U.S. PATENT DOCUMENTS

2016/0310482 A1* 10/2016 Haber .................... A61P 43/00

FOREIGN PATENT DOCUMENTS

WO WO2016/141324 9/2016

OTHER PUBLICATIONS

Gerdes et al. Emerging understanding of multiscale tumor heterogeneity, Front. Oncol. Dec. 18, 2014 doi: 10.3389/fonc.2014.00366, pp. 1-12 (Year: 2014).*
Gura, T., Systems for Identifying New Drugs Are Often Faulty, Science, 1997, 278:1041-1042 (Year: 1997).*
Kaiser, J., First pass at cancer genoome reveals complex landscape, Science, 2006, 313:1370 (Year: 2006).*
Braghiroli et al., Genomic profiling and efficacy of anti-EGFR therapy in appendiceal adenocarcinoma., Journal of Clinical Oncology 34, No. 15-suppl, p. 4102, Publication Date: May 20, 2016 (Year: 2016).*
Pao et al., Rational, biologically based treatment of EGFR-mutant non-small-cell lung cancer, Nature Reviews, Cancer, vol. 10, 760-774, Publication Year: 2010 (Year: 2010).*
Amatu et al., NTRK gene fusions as novel targets of cancer therapy across multiple tumour types, ESMO Open 2016; 1:e000023, Publication Date: Mar. 18, 2016 (Year: 2016).*
Yun et al., The T790M mutation in EGFR kinase causes drug resistance by increasing the affinity for ATP, PNAS, vol. 105, 6, 2070-2075, Publication Date: Feb. 12, 2008 (Year: 2008).*
Regales et al., Dual targeting of EGFR can overcome a major drug resistance mutation in mouse models of EGFR mutant lung cancer, J. Clin. Invest. 119:3000-3010, Publication Date: Oct. 2009 (Year: 2009).*
Matsui et al., EK•B-569: An6 Irreversib2le EGFR b•/rosins k Inass inhibitor, Abstract of the 11th World Conference on Lung Cancer, Jul. 3-6, 2005, Barcelona, Spain (Year: 2005).*
Pawlick, T.M. et al., "Colorectal carcinogenesis: MSI-H versus MSI-L", Dis. Markers, 2004, 20:199-206.
Berg, M. and Soreide, K., "Genetic and epigenetic traits as biomarkers in colorectal cancer", Int'l. J. Mol. Science, 2011, 12:9426-9439.
Boland, C.R. and Goel, A., "Microsatellite instability in colorectal cancer", Gastroenterology, 2010, 138:2073-2087.
Richman, S."Deficient mismatch repair: Read all about it (Review)", Int'l. J. Oncol., 2015, 47:1189-1202.
Vilar, E. and Gruber, S.B., "Microsatellite instability in colorectal cancer-the stable evidence", Nat. Rev. Clin. Oncol., 2010, 7:153-162.
Cancer Genome Atlas Network, "Comprehensive molecular characterization of human colon and rectal cancer", Nature, 2012, 487:330-337.
Timmermann. B. et al., "Somatic mutation profiles of MSI and MSS colorectal cancer identified by whole exome next generation sequencing and bioinformatics analysis", PLoS One, 2010, 5:e15661.
Zhang, Y. et al., "Involvement of Nucleotide Excision and Mismatch Repair Mechanisms in Double Strand Break Repair", Curr. Genomics, 2009, 10:250-258.

(Continued)

*Primary Examiner* — Peter J Reddig
*Assistant Examiner* — Cheng Lu
(74) *Attorney, Agent, or Firm* — Armstrong Teasdale LLP

(57) ABSTRACT

The present disclosure provides methods for identifying subjects having a cancer or tumor that may be susceptible to treatment with a therapeutic agent used to EGFR-related cancer an/or NTRK-related cancer.

14 Claims, 33 Drawing Sheets
(26 of 33 Drawing Sheet(s) Filed in Color)
Specification includes a Sequence Listing.

(56) References Cited

OTHER PUBLICATIONS

By, O. et al., "Epidermal growth factor receptor mutations in colorectal cancer patients", J Korean Soc. Coloproctol, 2011, 27:127-132.

Shi, C. and Washington, K., "Molecular testing in colorectal cancer: diagnosis of Lynch syndrome and personalized cancer medicine", Am. J. Clin. Pathol., 2012, 137:847-859.

Shigematsu, H. et al., "Clinical and biological features associated with epidermal growth factor receptor gene mutations in lung cancers", J. Nat'l. Cancer Inst., 2005, 97:339-346.

Nagahara, H et al., "Somatic mutations of epidermal growth factor receptor in colorectal carcinoma", Clin. Cancer. Res., 2005, 11:1368-1371.

Li, B. et al., "Automated inference of molecular mechanisms of disease from amino acid substitutions", Bioinformatics, 2009, 25:2744-2750.

Bond, C.E. et al., "p53 mutation is common in microsatellite stable, BRAF mutant colorectal cancers", Int'l. J. Cancer, 2012, 130:1567-1576.

Shaib, W. et al., "Markers of resistance to anti-EGFR therapy in colorectal cancer", J. Gastrointest. Oncol., 2013, 4:308-318.

U, M. et al., "Prediction and prioritization of rare oncogenic mutations in the cancer Kinome using novel features and multiple classifiers", PLoS Comput. Biol., 2014, 10:e1003545.

Torkamani, A. and Schork, N.J., "Prediction of cancer driver mutations in protein kinases", Cancer Research, 2008, 68:1675-1682.

Pao, W. et al., "Acquired resistance of lung adenocarcinomas to gefitinib or erlotinib is associated with a second mutation in the EGFR kinase domain", PLoS Med., 2005, 2:e73.

Corso, G. et al., "Oncogenic mutations and microsatellite instability phenotype predict specific anatomical subsite in colorectal cancer patients", European Journal of Human Genetics, 2013, 21(12):1383-1388.

\* cited by examiner

A) MSI-H group

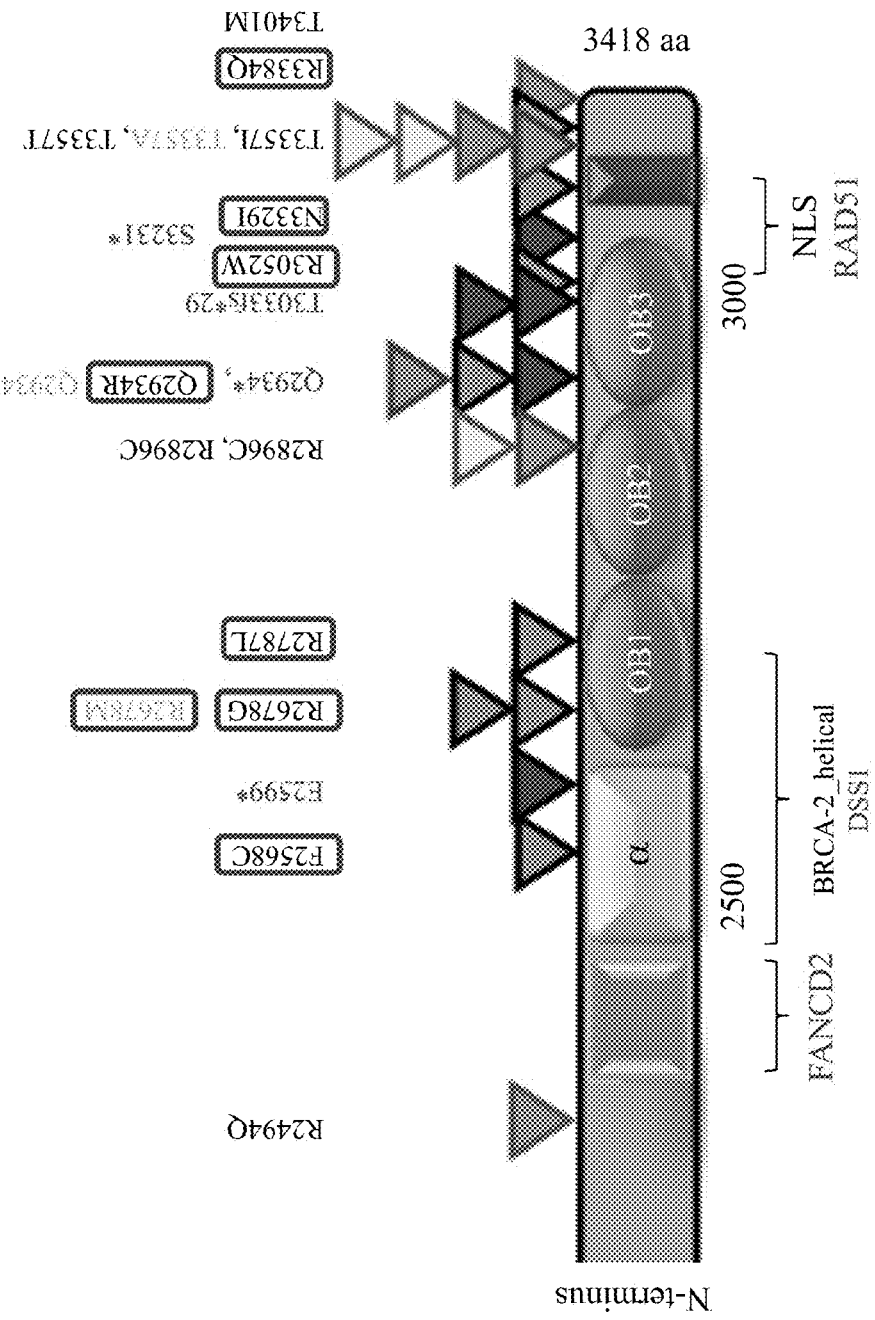

C)

SEQUENCE LISTING

```
<160> NUMBER OF SEQ ID NOS: 9

<210> SEQ ID NO 1
<211> LENGTH: 10
<212> TYPE: DNA
<213> ORGANISM: artificial sequence
<220> FEATURE:
<223> OTHER INFORMATION: Polynucleotide repeats in coding BRCA2

<400> SEQUENCE: 1
aaaaaaaaaa                                                              10

<210> SEQ ID NO 2
<211> LENGTH: 10
<212> TYPE: DNA
<213> ORGANISM: artificial sequence
<220> FEATURE:
<223> OTHER INFORMATION: Polynucleotide repeats in coding BRCA2

<400> SEQUENCE: 2
tttttttttt                                                              10

<210> SEQ ID NO 3
<211> LENGTH: 10
<212> TYPE: DNA
<213> ORGANISM: artificial sequence
<220> FEATURE:
<223> OTHER INFORMATION: Polynucleotide repeats in coding BRCA2

<400> SEQUENCE: 3
ccaccaccac                                                              10

<210> SEQ ID NO 4
<211> LENGTH: 42
<212> TYPE: DNA
<213> ORGANISM: artificial sequence
<220> FEATURE:
<223> OTHER INFORMATION: Polynucleotide splicing cite coding BRCA2

<400> SEQUENCE: 4
ttctgtttta tactttaaca ggatttggaa aaacatcagg ga                          42

<210> SEQ ID NO 5
<211> LENGTH: 14
<212> TYPE: PRT
<213> ORGANISM: artificial sequence
<220> FEATURE:
<223> OTHER INFORMATION: splicing cite coding BRCA2

<400> SEQUENCE: 5

Ser Val Leu Tyr Phe Asn Arg Ile Trp Lys Asn Ile Arg Glu
1               5                   10

<210> SEQ ID NO 6
<211> LENGTH: 14
<212> TYPE: PRT
<213> ORGANISM: artificial sequence
```

```
<220> FEATURE:
<223> OTHER INFORMATION: splicing cite coding BRCA2

<400> SEQUENCE: 6

Leu Leu Phe Tyr Thr Leu Thr Gly Phe Gly Lys Thr Ser Gly
1               5                   10

<210> SEQ ID NO 7
<211> LENGTH: 5
<212> TYPE: PRT
<213> ORGANISM: artificial sequence
<220> FEATURE:
<223> OTHER INFORMATION: splicing cite coding BRCA2

<400> SEQUENCE: 7

Phe Cys Phe Ile Cys
1               5

<210> SEQ ID NO 8
<211> LENGTH: 8
<212> TYPE: PRT
<213> ORGANISM: artificial sequence
<220> FEATURE:
<223> OTHER INFORMATION: splicing cite coding BRCA2

<400> SEQUENCE: 8

Gln Asp Leu Glu Lys His Gln Gly
1               5

<210> SEQ ID NO 9
<211> LENGTH: 7
<212> TYPE: PRT
<213> ORGANISM: artificial sequence
<220> FEATURE:
<223> OTHER INFORMATION: splicing cite coding BRCA2

<400> SEQUENCE: 9

Gly Phe Gly Lys Thr Ser Gly
1               5
```

FREQUENT EGFR AND NTRK SOMATIC MUTATIONS IN COLORECTAL CANCER (CRC) WITH MICROSATELLITE INSTABILITY (MSI)

REFERENCE TO GOVERNMENT GRANTS

This invention was made with government support under RP-14-233-07 awarded by the Other Agency, and CA006927 awarded by the National Institutes of Health. The government has certain rights in the invention.

REFERENCE TO SEQUENCE LISTING

This application includes a Sequence Listing submitted electronically as a text file named 853003225SEQ, created on Aug. 7, 2023, with a size of 2,318 bytes. The Sequence Listing is incorporated herein by reference.

FIELD

The present disclosure is directed, in part, to methods for identifying subjects having a cancer or tumor that may be susceptible to treatment with a therapeutic agent used to treat EGFR-related cancer and/or NTRK-related cancer.

BACKGROUND

Colorectal cancer (CRC) incidence and mortality rates are remarkably high worldwide, with 1.4 million new cases and approximately 700,000 deaths per year (Torre et al., CA Cancer J. Clin., 2015, 65, 87-108). With the rapid increase, the global incidence and mortality rate of CRC is predicted to undergo a 60% rise by 2030 (Arnold et al., Gut, 2017, 66, 683-691). CRCs arise through genetic changes that impact various driver genes and in some tumors increased mutation rate occurs in microsatellite unstable tumors (Pawlik et al., Dis. Markers, 2004, 20, 199-206; and Berg et al., Int'l. J. Mol. Sciences, 2011, 12, 9426). A hypermutable phenotype associated with microsatellite instability (MSI) results from loss of the mismatch repair (MMVR) activity (Boland et al., Gastroenterol., 2010, 138, 2073-2087; and Richman, Int'l. J. Oncol., 2015, 47, 1189-1202). MSI is detected in a small fraction (<15%) of all CRCs, and such tumors have a better prognosis and different chemotherapeutic sensitivities as compared to non-MSI tumors (Pawlik et al., Dis. Markers, 2004, 20, 199-206; and Berg et al., Int'l. J. Mol. Sciences, 2011, 12, 9426; Boland et al., Gastroenterol., 2010, 138, 2073-2087; and Richman, Int'l. J. Oncol., 2015, 47, 1189-1202; Vilar et al., Nat. Rev. Clin. Oncol., 2010, 7, 153-162; and Cancer Genome Atlas Network, Nature, 2012, 487, 330-337).

Approximately 90% of hereditary non-polyposis colorectal cancer (HPNCC) patients are reported to harbor germline mutations in MLH1 and MSH2 (Pawlik et al., Dis. Markers, 2004, 20, 199-206; and Berg et al., Int'l. J. Mol. Sciences, 2011, 12, 9426; and Timmermann et al., PLoS One, 2010, 5, e15661). Germ line, somatic and epigenetic inactivation of the MMR genes MLH1 and MSH2 results in complete loss of MMR leading to oncogenesis, recognized as an MSI-H state both sporadically and in HPNCC (Pawlik et al., Dis. Markers, 2004, 20, 199-206; and Berg et al., Int'l. J. Mol. Sciences, 2011, 12, 9426; and Zhang et al., Curr. Genomics., 2009, 10, 250-258). A distinct MSI phenotype with a low level of the MMR markers MSH3, MSH6, PMS1 and PMS2 is known as the MSI-Low (MSI-L) CRC subtype with a weak effect on MMR system failure (Pawlik et al., Dis. Markers, 2004, 20, 199-206; and Berg et al., Int'l. J. Mol. Sciences, 2011, 12, 9426; Boland et al., Gastroenterol., 2010, 138, 2073-2087; and Richman, Int'l. J. Oncol., 2015, 47, 1189-1202). The MMR pathway is believed not only to function as one of the most essential systems for maintenance of genome integrity, but also to mediate DNA double-strand break (DSB) repair (Zhang et al., Curr. Genomics., 2009, 10, 250-258). Various studies have suggested a modulator effect of MSH2 and MLH1 in homologous recombination (HR) (Zhang et al., Curr. Genomics., 2009, 10, 250-258; and Elliott et al., Mol. Cell. Biol., 2001, 21, 2671-2682). Delays in the recruitment of RAD51 and MRE11 to DNA damage sites, and failed repair of DNA DSBs mediated by gene conversion is observed in MSH2-deficient colorectal cancer cells (Zhang et al., Curr. Genomics., 2009, 10, 250-258; and Elliott et al., Mol. Cell. Biol., 2001, 21, 2671-2682). Ionizing radiation can induce a high frequency of mitotic recombination in MLH1-null cells (Zhang et al., Curr. Genomics., 2009, 10, 250-258; and Wang et al., Mutat. Res., 2006, 594, 189-198). How mechanistically MSH2 and MLH1 impact on DSB repair and HR factors remains to be fully understood (Kobayashi et al., Oncol. Rep., 2013, 30, 1019-1029).

Repetitive DNA sequences are more prone to mutation in tumors with MMR deficiency (Vilar et al., Nat. Rev. Clin. Oncol., 2010, 7, 153-162). Coding microsatellites in HR factors hRAD50 and MRE11A can be mutated in MSI tumors and are reported to sensitize MSI tumors to PARP-1 inhibitors (Vilar et al., Nat. Rev. Clin. Oncol., 2010, 7, 153-162). Repetitive sequences within the Bax or TGF-beta Type II receptor genes have been reported to be mutated in MMR-deficient CRCs (Iacopetta et al., J. Pathol., 1999, 187, 428-432). The BRCA2 protein is a fundamental element of HR and 91 somatic mutations in BRCA2 are known cancer drivers (Sakopamig et al., PLoS Comput. Biol., 2015, 11, e1004027; and Cancer Genome Atlas Research Network, Nature, 2011, 474, 609-615). There is little evidence to suggest that BRCA2 is associated with increased risk of colon cancer although it is known that BRCA1 carriers have about a 3-fold increased risk of CRC (Phelan et al., Br. J. Cancer, 2014, 110, 530-4; and Sopik et al., Clin. Genet., 2015, 87, 411-418). The high frequency of repetitive sequences in BRCA2 could allow for frequent mutations in MSI tumors (Welcsh et al., Hum. Mol. Genet., 2001, 10, 705-713). Identification of somatic mutations in BRCA2 could provide a basis for therapy with PARP-1 inhibitors especially if the defects are biallelic (Hennessy et al., J. Clin. Oncol., 2010, 28, 3570-3576). We disclose herein that BRCA2 harboring high frequency of microsatellites may be a substrate for mutation and may lead to a driver phenotype in tumors that have lost their MMR system and there is a goal to acquire biallelic hits in BRCA2.

Epidermal growth factor receptor (EGFR), a member of ErbB family, is a transmembrane glycoprotein that forms a receptor tyrosine kinase (Shaib et al., J. Gastrointest. Oncol., 2013, 4, 308-318; and Oh et al., J. Korean Soc. Coloproctol., 2011, 27, 127-32). EGFR overexpression is associated with tumorigenesis and malignancy of many epithelial tumors including MSI colon cancer through activation of downstream signaling pathways involving RAS-RAF-MAPK and PTEN-PI3K-AKT (Oh et al., J. Korean Soc. Coloproctol., 2011, 27, 127-32; and Shi et al., Am. J. Clin. Pathol., 2012, 137, 847-859). EGFR mutations in the tyrosine kinase domain occur in about 10% of Non-small cell lung cancer (NSCLC), sensitize the patients' tumors to tyrosine kinase inhibitors (TKI) (Shigematsu et al., J. Nat'l. Cancer Inst., 2005, 97, 339-346). These patients are typically non-smokers, female and of Asian descent. There are limited reports on the incidence rate of EGFR mutation in colorectal patients (Oh et al., J. Korean Soc. Coloproctol., 2011, 27, 127-32; and Nagahara et al., Clin. Cancer Res., 2005, 11, 1368-7122).

SUMMARY

The present disclosure provides methods for diagnosing and treating a cancer or tumor having high microsatellite instability in a subject in need thereof, comprising: analyzing a sample from the subject for the presence or absence of one or more mutations in EGFR and/or NTRK, wherein the subject is diagnosed with a cancer or tumor having high microsatellite instability if the one or more mutations in EGFR and/or NTRK are detected; and administering a therapeutic agent to the diagnosed subject, wherein the therapeutic agent is an agent used to treat EGFR-related cancer and/or NTRK-related cancer.

The present disclosure also provides methods for treating cancer or tumor having high microsatellite instability in a subject in need thereof, comprising: requesting a test providing the results of an analysis of a sample from the subject for the presence or absence of one or more mutations in EGFR and/or NTRK, wherein the subject is diagnosed with a cancer or tumor having high microsatellite instability if the one or more mutations in EGFR and/or NTRK are detected; and administering a therapeutic agent to the diagnosed subject, wherein the therapeutic agent is an agent used to treat EGFR-related cancer and/or NTRK-related cancer.

The present disclosure also provides methods for diagnosing cancer or tumor having high microsatellite instability in a subject, wherein the subject is diagnosed with a cancer or tumor having high microsatellite instability if the one or more mutations in EGFR and/or NTRK are detected, comprising: obtaining a sample from the subject; performing immunohistochemistry, sequencing, and/or microsatellite instability analysis on the sample to identify a high microsatellite instability; detecting one or more mutations in EGFR and/or NTRK; and diagnosing cancer or tumor having high microsatellite instability in a subject, wherein the subject is diagnosed with a cancer or tumor having high microsatellite instability if the one or more mutations in EGFR and/or NTRK are detected.

The present disclosure also provides methods for treating cancer or tumor having high microsatellite instability in a subject in need thereof, comprising: analyzing a sample from the subject for the presence or absence of one or more mutations in EGFR and/or NTRK; and administering a therapeutic agent to the diagnosed subject, wherein the therapeutic agent is an agent used to treat EGFR-related cancer and/or NTRK-related cancer.

The present disclosure also provides methods for identifying a subject having a cancer or tumor that may be susceptible to treatment with a therapeutic agent used to treat EGFR-related cancer and/or NTRK-related cancer, comprising: analyzing a sample from the subject for the presence or absence of one or more mutations in EGFR and/or NTRK; wherein the subject is diagnosed with the cancer or tumor having high microsatellite instability related to one or more mutations in EGFR and/or NTRK, wherein the subject may be susceptible to treatment with a therapeutic agent used to treat EGFR-related cancer and/or NTRK-related cancer.

Any of the methods disclosed herein can be carried out as described further below and can be carried out using any of the features described in greater detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

Figure 1:
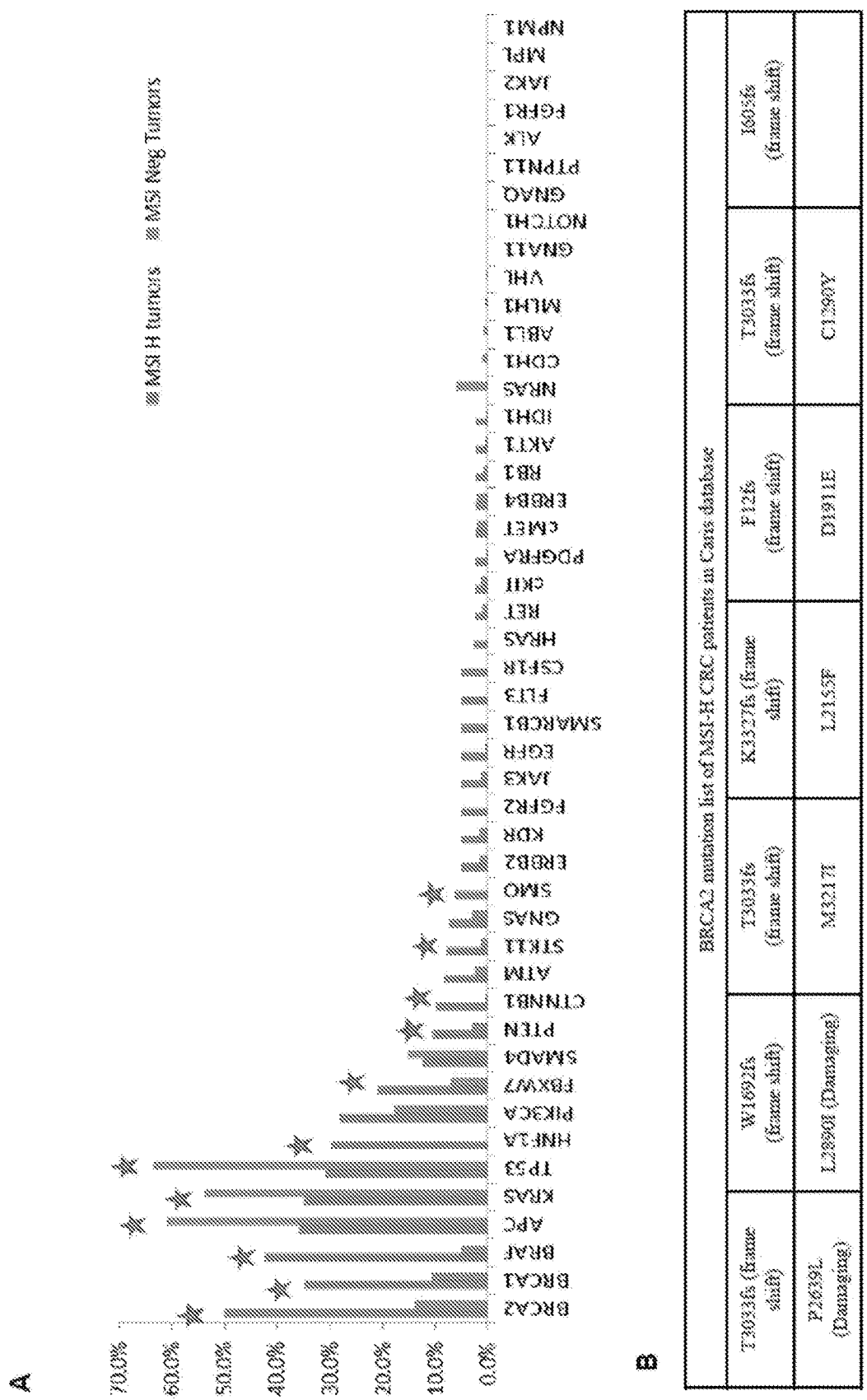
FIG. 1 (Panels A and B): BRCA2 is highly mutated in MSI-H CRCs in an initial cohort of CRCs profiled by Caris Life Sciences. (Panel A) Selected genes including deregulated genes in CRC in MSI-H and non-MSI-H CRC subtypes is plotted with different mutation frequencies among the MSI-H and non-MSI-H groups are shown. The p-value<0.01 shows the significance of the comparison, represented by stars. (Panel B) Damaging mutations including frameshift and missense mutations in MSI-H CRCs from the Caris dataset are listed in the table.

Microsatellite instability (MSI) is a hallmark of deficient mismatch repair (MMVR) and contributes to about 15% of colorectal cancer (CRCs). While progress has been made with immunotherapy to treat advanced disease, additional therapeutic strategies are needed for patients who experience disease progression.

A disclosed herein, MSI can lead to mutations in proteins involved in double strand break repair including BRCA2 and cancer drivers such as EGFR. We analyzed gene mutation frequencies among the cohorts in 26 MSI-High (MSI-H) and 558 non-MSI-H CRCs that were profiled at Caris Life Sciences. A second cohort from COSMIC including 101 MSI-H and 916 non-MSI-H CRCs was analyzed.

The Caris MSI-H CRCs had a significantly high mutation rate (50% vs 14% in non-MSI-H, P<0.0001) in BRCA2. Of 1104 profiled CRCs in the COSMIC v73 database, MSI-H CRCs showed a significantly higher mutation rate in BRCA2 as compared to non-MSI-H (38% vs 6%, P<0.0000001) with enrichment in coding microsatellites. EGFR was mutated in 45.5% of MSI-H and 6.5% of non-MSI-H tumors (P<0.0000001). Approximately 10-15% of the EGFR mutations found may be actionable through TKI therapy, including the N700D, G719D, T725M, T790M, and E884K EGFR mutants. BRCA2 mutations in MSI-H CRCs included 75 unique novel mutations not known as somatic mutations in either breast cancer or pancreatic cancer per COSMIC v73. The BIC database (world wide web at "research.nhgri.nih.gov/bic/") identified 5 BRCA2 deleterious mutations that have been reported as germ-line mutations in breast cancer. Five predictors and available 3-D structural information were used to predict deleterious properties of BRCA2 mutations including disruption of interactions with partner proteins DSS1 and RAD51. Some CRCs harbored multiple BRCA2 mutations.

A significant increase in BRCA2 and EGFR mutations occurs in MSI-H CRCs. The findings have immediate clinical relevance with regard to therapeutic targeting of BRCA2 vulnerabilities, EGFR mutations or other identified oncogenic drivers in MSI-H CRCs and other tumors with MSI.

The present disclosure provides methods for diagnosing and treating a cancer or tumor having high microsatellite instability in a subject in need thereof, comprising: analyzing a sample from the subject for the presence or absence of one or more mutations in EGFR and/or NTRK, wherein the subject is diagnosed with a cancer or tumor having high microsatellite instability if the one or more mutations in EGFR and/or NTRK are detected; and administering a therapeutic agent to the diagnosed subject, wherein the therapeutic agent is an agent used to treat EGFR-related cancer and/or NTRK-related cancer.

The present disclosure also provides methods for treating cancer or tumor having high microsatellite instability in a subject in need thereof, comprising: requesting a test providing the results of an analysis of a sample from the subject for the presence or absence of one or more mutations in EGFR and/or NTRK, wherein the subject is diagnosed with a cancer or tumor having high microsatellite instability if the one or more mutations in EGFR and/or NTRK are detected; and administering a therapeutic agent to the diagnosed subject, wherein the therapeutic agent is an agent used to treat EGFR-related cancer or NTRK-related cancer.

The present disclosure also provides methods for diagnosing cancer or tumor having high microsatellite instability in a subject, wherein the subject is diagnosed with a cancer or tumor having high microsatellite instability if the one or more mutations in EGFR and/or NTRK are detected, comprising: performing immunohistochemistry, sequencing, and/or microsatellite instability analysis on a sample obtained from the subject to identify a high microsatellite instability; detecting one or more mutations in EGFR and/or NTRK; and diagnosing cancer or tumor having high microsatellite instability in a subject, wherein the subject is diagnosed with a cancer or tumor having high microsatellite instability if the one or more mutations in EGFR and/or NTRK are detected.

The present disclosure also provides methods for treating cancer or tumor having high microsatellite instability in a subject in need thereof, comprising: analyzing a sample from the subject for the presence or absence of one or more mutations in EGFR and/or NTRK; and administering a therapeutic agent to the diagnosed subject, wherein the therapeutic agent is an agent used to treat EGFR-related cancer or NTRK-related cancer.

The present disclosure also provides methods for identifying a subject having a cancer or tumor that may be susceptible to treatment with a therapeutic agent used to treat EGFR-related cancer or NTRK-related cancer, comprising: analyzing a sample from the subject for the presence or absence of one or more mutations in EGFR and/or NTRK; wherein the subject is diagnosed with the cancer or tumor having high microsatellite instability related to one or more mutations in EGFR and/or NTRK, wherein the subject may be susceptible to treatment with a therapeutic agent used to treat EGFR-related cancer or NTRK-related cancer.

In any of the embodiments described herein, the sample is a biopsy from the subject. In some embodiments, the sample is a tumor biopsy from the subject.

In any of the embodiments described herein, the detection of one or more mutations in EGFR and/or NTRK can be carried out by, for example, performing immunohistochemistry, sequencing, and/or microsatellite instability analysis on a sample obtained from the subject. Performance of immunohistochemistry, sequencing, and/or microsatellite instability analysis on a sample obtained from the subject can be compared to samples or sequence information from wild type EGFR and/or NTRK. Suitable examples of the detection of one or more mutations in EGFR and/or NTRK can be found, for instance, in the examples presented below. In any of the embodiments described herein, the mutation in EGFR is N700D, G719D, T725M, T790M, and/or E884K. In any of the embodiments described herein, the mutation in NTRK is: I699V in NTRK1, P716S in NTRK2, or R745L in NTRK3.

In any of the embodiments described herein, the therapeutic agent is a chemotherapeutic agent. In some embodiments, the chemotherapeutic agent is a tyrosine kinase inhibitor. In some embodiments, the therapeutic agent is an antibody, such as Cetuximab or Panitumumab, or a small molecule, such as Erlotinib, Gefitinib, or Osimertinib. The amount of the particular therapeutic agent administered can be the standard amount of such therapeutic agent that is currently administered to cancer patients.

In any of the embodiments described herein, the cancer or tumor is colorectal cancer.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1: Material and Methods

Microsatellite Status Determination

Our initial cohort included 26 MSI-H and 558 microsatellite stable (MSS) cases that were profiled at Caris Life Sciences (Phoenix, AZ) using immunohistochemistry (IHC) and sequencing (NextGen and Sanger). MSI status was determined using a combination of IHC (MLH1, PMS2, MSH2, MSH6) and MIA (Microsatellite Instability Analysis) fragment analysis. MIA included fluorescently-labeled primers for co-amplification of seven markers including five mononucleotide repeat markers (BAT-25, BAT26, NR-21, NR24 and MONO-27) and two pentanucleotide repeat markers (Penta C and D). The mononucleotide markers were used for MSI determination while the pentanucleotide markers were used to detect either sample mix-ups or contamination. A sample was considered MSI-H if two or more mononucleotide repeats were abnormal while MSI-L if one mononucleotide repeat was abnormal. The tumors were considered MSS if mononucleotide repeats were identical between the tumor and adjacent normal tissue.

Bioinformatics Workflow

We downloaded the full Cosmic V73 whole-genome data and TCGA [COAD] level 3 expression data. The COSMIC data was filtered by selecting all mutations occurring in the large intestine, excluding mutations flagged as SNPs, and removing duplicate mutations (i.e., identical mutations labeled with different transcripts). Annotation of variants was performed with Annovar (PMID 20601685), including deleteriousness prediction scores such as PolyPhen-2. Tissue-specific genes are picked and gene expression levels were confirmed with the TIGER (Tissue-specific Gene Expression and Regulation) database. Breast Cancer Information Core (BIC), an Open Access On-Line Breast Cancer Mutation Data Base, was applied to detect the previous identified BRCA2 mutations.

Statistical Analysis

Differences in sample proportions were compared using Fisher's exact tests. Wilcoxon rank sum tests were used to perform between comparisons of continuous variables including mutation counts between MSI-H and non-MSI-H samples. All statistical tests were 2-sided. Statistical significance was defined as $P<0.01$. Bonferroni adjustment for multiple comparisons was performed.

Functional Prediction Modeling

We used five predictors to predict BRCA2 mutations, including PolyPhen-2 (Polymorphism Phenotyping v2) (Adzhubei et al., Nat. Methods, 2010, 7, 248-249), SIFT (Sorting Intolerant From Tolerant) (Kumar et al., Nat. Ptotoc., 2009, 4, 1073-1081), PROVEAN (Protein Variation Effect Analyzer) (Choi et al., PLos One, 2012, 7, e46688), MutPred (Li et al., Bioinformatics, 2009, 25, 2744-2750), and a predictor using support vector machine (SVM) developed by Wei and Dunbrack (Wei et al., PLoS One, 2013, 8, e67863). These methods are trained on existing sets of mutation/phenotype association data and use sequence information from homologues, structure information, such as accessible surface area, and changes in amino acid properties to provide feature information as input to machine learning methods for phenotype prediction. PolyPhen-2 provides the probability of being deleterious. If the probability is less than 0.5, the mutation is considered to be "benign", otherwise, it is considered as "probably damaging". SIFT outputs a normalized probability for each amino acid type, and a value of less than 0.05 is considered deleterious. PROVEAN uses an alignment-based score that measures the variation of a query sequence and its homolog before and after mutation. The cutoff is −2.5 where PROVEAN has best specificity and sensitivity. A value of less than −2.5 is considered deleterious. MutPred provides probabilities of gain or loss of structure and function. We used 0.5 as cutoff, a value of less than 0.5 is considered deleterious. The SVM predictor used both sequence and structural information, trained on balanced data sets of 496 deleterious and neutral mutations. The SVM predictor also yields probabilities where a value >0.5 is considered as deleterious. We used BioAssemblyModeler (BAM) (Shapovalov et al., PLoS One, 2014, 9, e98309) software to do homology modelin: first backbone atoms are copied from template structure, STK11, and SMO. The specific deleterious BRCA2 mutations found in the Caris dataset in MSI-H CRCs are listed in FIG. 1, Panel B. Among the frameshift BRCA2 mutations in MSI-H CRCs, 4 (50%) were found in repetitive sequences of the BRCA2 gene. Common MSI-associated mutations in other genes detected in the Caris life sciences dataset include FLCN (H429fs), HNF1A (P291fs), PTEN (K267fs, N323fs, T319fs), RNF43 (G659fs), and MSH6 (F1088fs; occurs in tumors that are already MSI).

We further derived mutation data from the Catalog of Somatic Mutations in Cancer (COSMIC) database and The Cancer Genome Atlas (TCGA) data set (Cancer Genome Atlas Network, Nature, 2012, 487, 330-337; and Li et al., Bioinformatics, 2009, 25, 2744-2750). To profile and assess the potentially destructive mutations in BRCA2, we evaluated 101 MSI-H and 916 non-MSI-H profiled samples with various prediction algorithms for their BRCA2 functionally important somatic mutations (see, Table 1).

TABLE 1

Molecular characteristics of defined cohorts from different databases.

| | | | MSI-H CRCs | non-MSI-H CRCs |
|---|---|---|---|---|
| Caris Life Sciences | Samples Mutations | BRCA1 BRCA2 | 26 5 patients (Neutral) 13 patients (8/14 frameshift and 2/14 missense damaging mutations) | 558 28 Patients (Neutral) 79 patients |
| COSMIC (including TCGA data) | Samples Mutations | BRCA1 BRCA2 EGFR TP53 POLε | 101 28 patients (9/43 damaging mutations) 46 patients (48/75 damaging mutations) 46 patients (32/75 damaging mutations targeting TK domain) 68 patients (6/137 damaging mutations targeting hotspots) 43 patients (25 damaging) | 916 45 patients (4/48 damaging mutations) 58 patients (25/58 damaging mutation) 60 patients (30/80 damaging mutations targeting TK domain) 542 patients (194/606 damaging mutations targeting hotspots) 39 patients (21 damaging) | then side-chain coordinates are built from with the program SCWRL4 (Krivov et al., Proteins, 2009, 77, 778-795). We used YASARA web site (Krieger et al., Proteins, 2009, 77, 114-122) (world wide web at "yasara.org/minimization-server.htm") to perform energy minimization using the YASARA force field. All structures were studied in PyMOL (world wide web at "pymol.org/").

Example 2: Initial Cohort of CRC Analyzed by Genomic Profiling Identifies Frequent BRCA2 Mutations in MSI-H Tumors We analyzed the mutation data for 26 MSI-H and 558 non-MSI-H CRCs that were profiled at Caris Life Sciences. The MSI-H CRCs showed a significantly higher mutation frequency in the BRCA2 gene as compared to the non-MSI-H tumors (50% vs 14%, P<0.0001) (see FIG. 1, Panels A and B). In the Caris cohort, there was enrichment for BRCA2, BRCA1, and BRAF mutations in MSI-H CRCs while APC, KRAS, and p53 mutations appeared significantly reduced. Additional rarely mutated genes appeared to be significantly increased in MSI-H tumors in the Caris dataset including HNF1A, FBXW7, PTEN, CTNNB1, Example 3: Somatic Alterations within MLH1 and MSH2 Proteins Found in MSI-H Patient Tumors The COSMIC v73 dataset has profiled patients with cancers including patients with cancer in their large intestine, displaying sequenced genes with mutations (Wei et al., PLoS One, 2013, 8, e67863). The mutation collections for the large intestine in the present study were derived from the COSMIC whole genome version 73. Analyzing exome sequences, the COSMIC whole genome database profiled 1104 samples with CRCs for their somatic mutations in coding exons (Cancer Genome Atlas Network, Nature, 2012, 487, 330-337). Since microsatellite status (MS) is not available in the COSMIC, we designed a cohort with bioinformatics tools to define the MS status regarding the potential loss of function in MMR proteins. We defined coding variations with functional impact on corresponding protein as pathogenic or benign as predicted by the FATHMM online server (word wide web at "fathmm.biocompute.org.uk/"). PolyPhen-2 (world wide web at "genetics.bwh.harvard.edu/pph2/") was applied to further verify damaging effect of missense mutations in MMR proteins.

Figure 2:
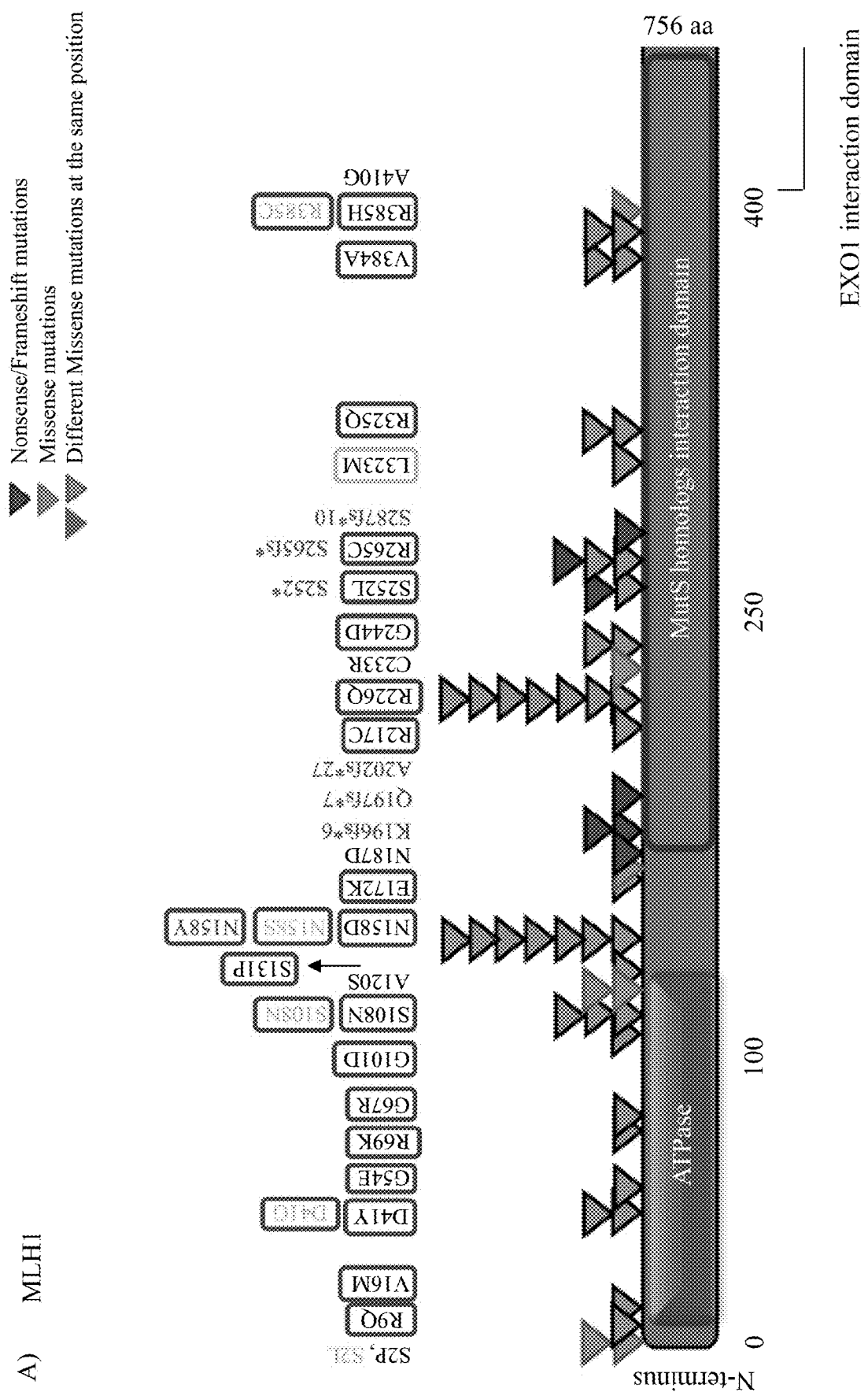
FIG. 2 (Panels A and B): MLH1 and MSH2 protein domains annotated with somatic non-synonymous alterations observed in MSI-H CRCs from the COSMIC database. (Panel A) MLH1 domains and variants. Three known domains are shown in the protein structure. The alterations including missense, nonsense and frameshift mutations are mapped with respect to known domains. Different numbers and colors of triangles in the same positions are representatives of frequency and diversity of mutations in the same spot, respectively. Red triangles represent the truncated mutations, while missense variants are shown in blue, brown and green. Variants predicted by PolyPhen-2 (world wide web at "genetics.bwh.harvard.edu/pph2/") to be damaging are denoted in black-outlined triangle as well as red/orange rectangle. Red rectangles are representative of damaging mutations with high probability (>90%) and orange rectangles outline the mutations with possibility (>50%). (Panel B) MSH2 domains and variants.
Figure 2:
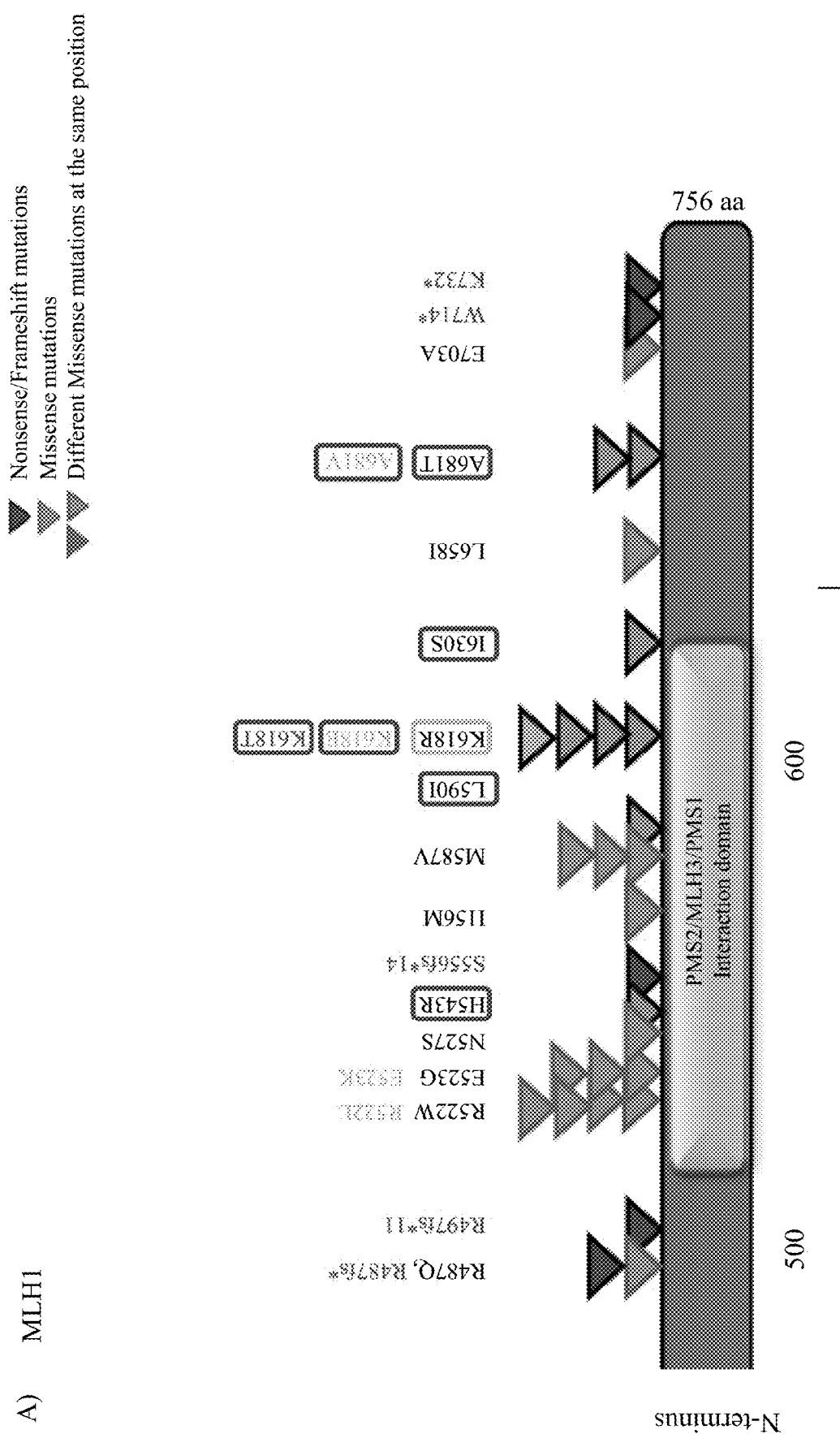
Figure 2:
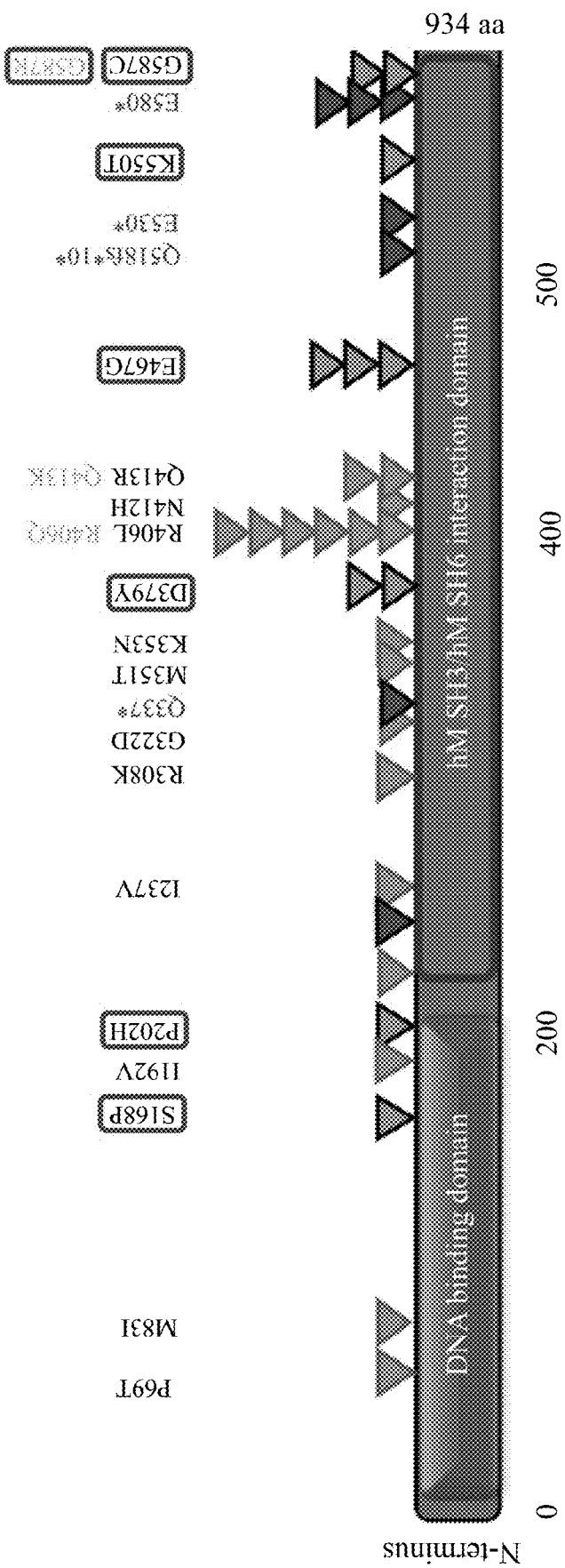
Figure 2:
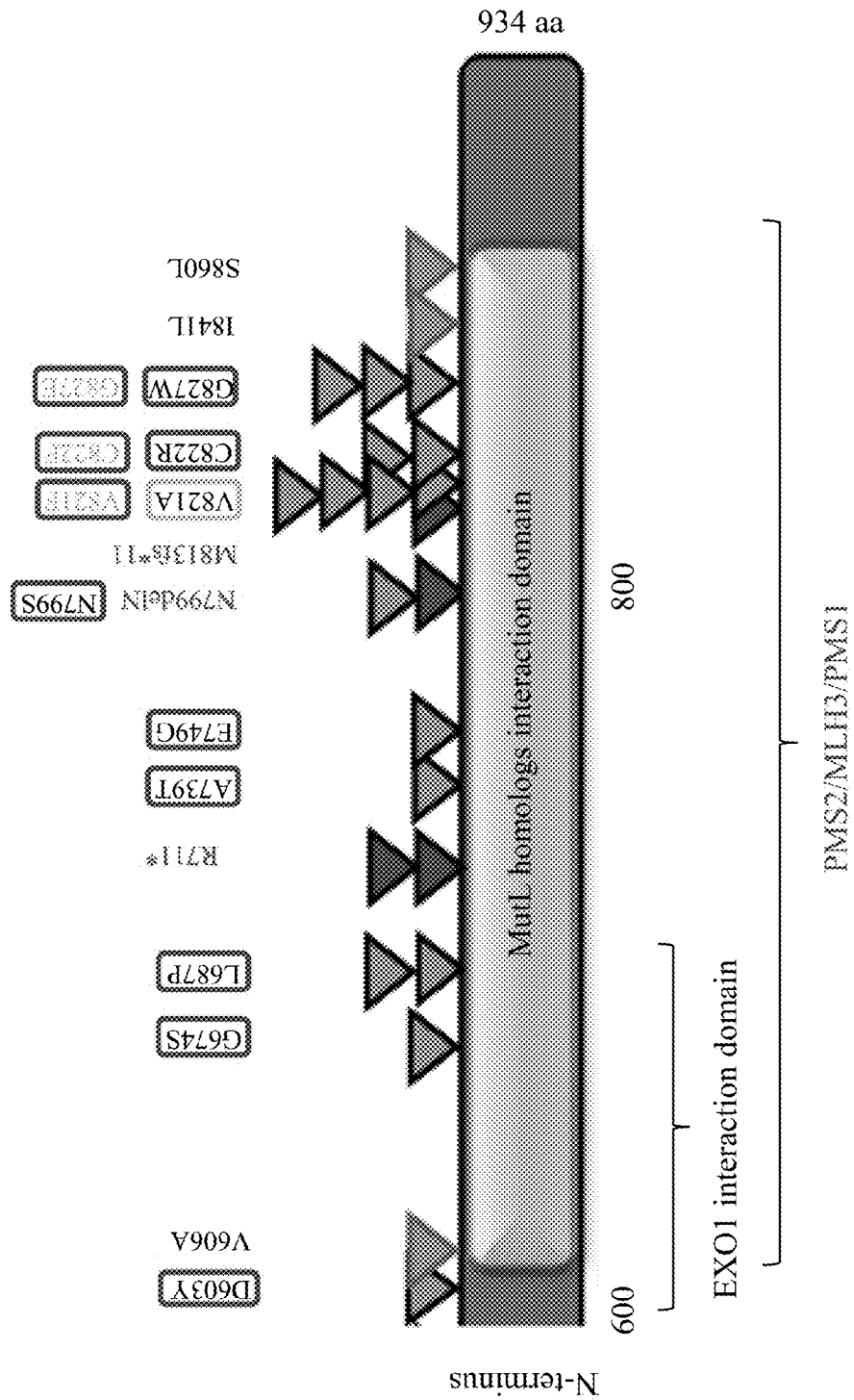
Figure 2:
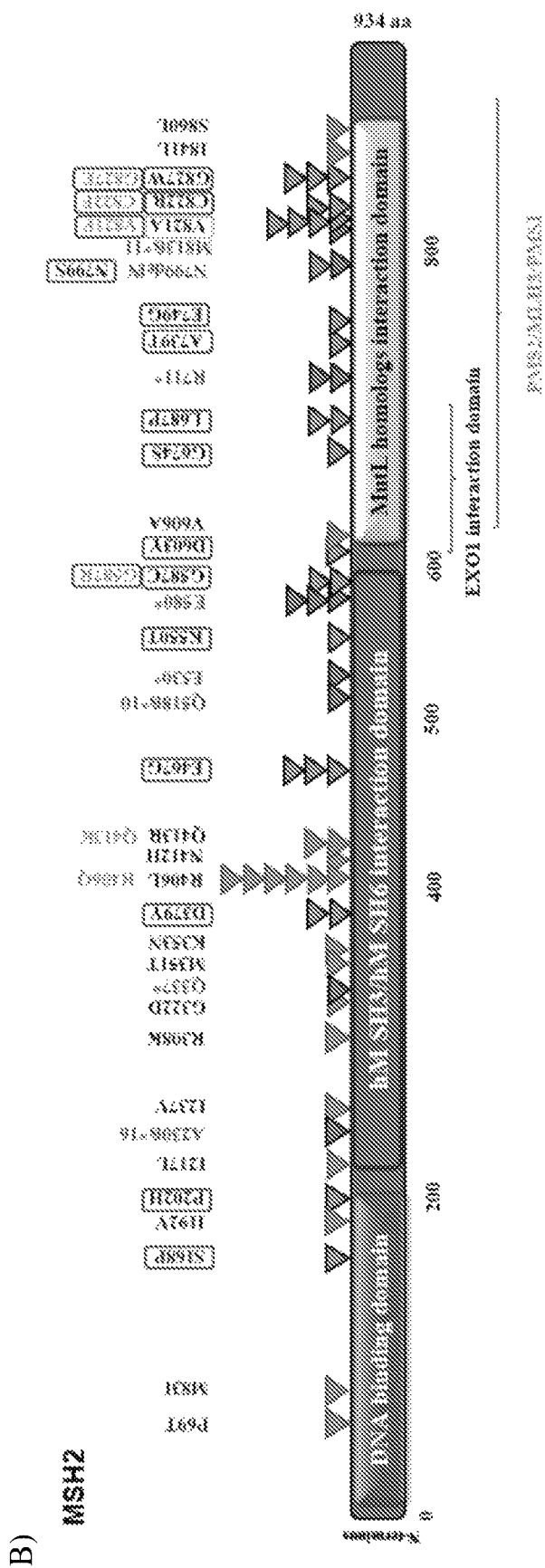
Figure 8:
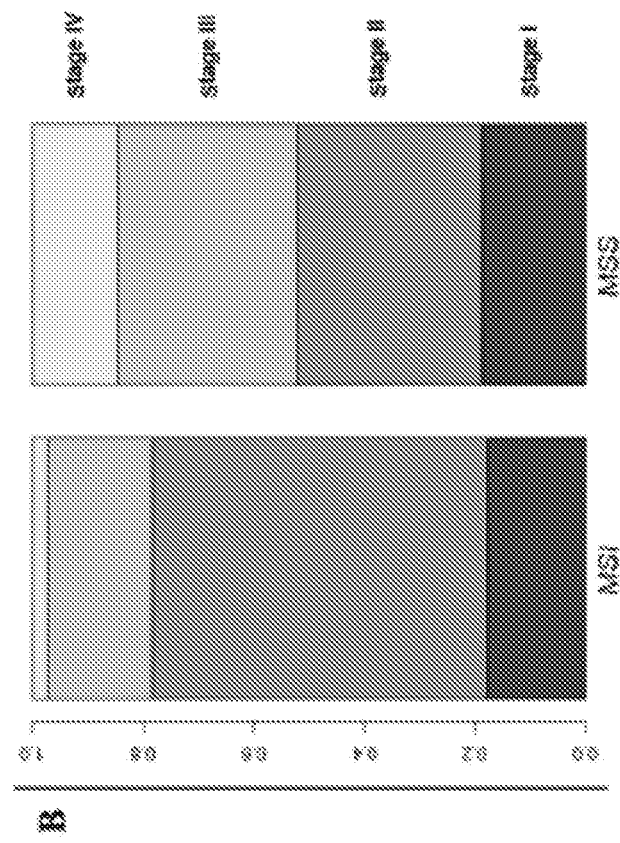
FIG. 8 (Panels A and B): 17% of CRCs, the predicted MSI cohort, has high frequency of stage II CRC. (Panel A) Distribution of CRC subtypes are plotted in the Pie chart. MSI includes both MSI-H and MSI-L populations. (Panel B) Distribution of CRC stages of both MSI and MSS groups in the cohort is plotted together.
Figure 8:
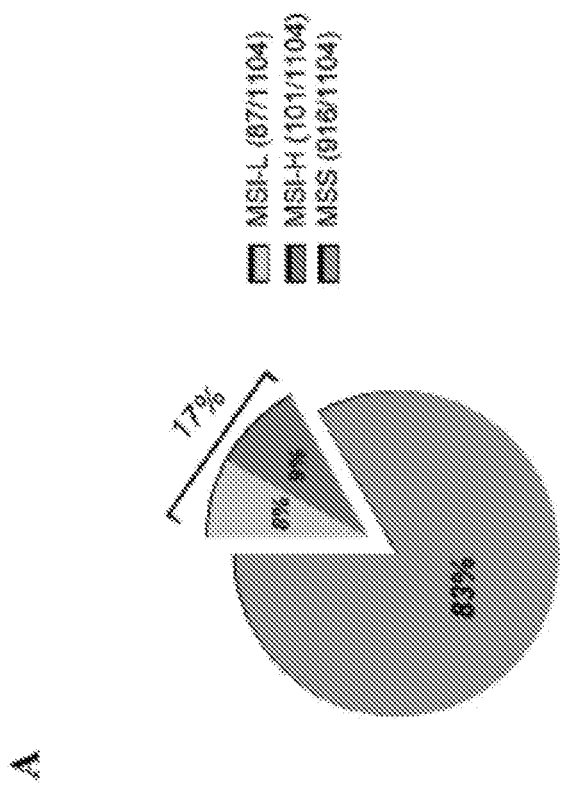

The MSI-H cohort was defined based on the presence of damaging mutations in MLH1 and MSH2. CRCs containing either wild-type or synonymous mutated MMR genes MLH1, MSH2, MSH3, MSH6, PMS1 and PMS2 were included in the non-MSI-H (MSS) cohort. Among the profiled CRC samples in the COSMIC version 73, 101 MSI-H and 916 non-MSI-H were categorized according to our definition. The MSI-L samples with no clear connection with defective MMR genes were excluded from our statistical analysis. Most of the mutations predicted to be pathogenic by FATHMM were also predicted to be damaging via the PolyPhen-2 algorithm, mapped on both MLH1 and MSH2 protein structures (see, FIG. 2, Panels A and B). Identified 155 MSI-H tumors exhibited at least one somatic mutation with a damaging effect in MLH1 or MSH-2 proteins in some cases was accompanied by other non-synonymous mutation(s) of MMR genes. The frequency of predicted MSI-H in the CRC population under study was observed at 17 percent (see, FIG. 8), similar to the reported prevalence of MSI in CRC. As expected, CRC patients with MSI are detected more among stage II and less in stage IV (see, FIG. 8). Moreover, $POL_E$ mutation frequency was significantly increased in MSI-H CRCs (42% vs. 4% in MSS, P<0.0000001) (see, Table 1), as expected in hypermutable tumors.

Example 4: BRCA2 is Among the Highly Mutated Genes in CRC Patients with Microsatellite Instability in a Validation Cohort from COSMIC Microsatellite testing provides a predictive marker to identify the underlying MMR mutations and this may correlate with the mutation rate in the cell (Timmermann et al., PLoS One, 2010, 5, e15661). We assessed the number of mutated genes in MSI-H and non-MSI-H tumors to determine whether MSI affects the number of mutated genes. A significantly higher rate of mutated genes in MSI-H CRCs vs. non-MSI-H (boxplot median 526 vs 101; P<0.0000001) was found corresponding to non-functional MLH1 and MSH2 proteins (see, FIG. 3, Panel A). According to prediction-based non-MSI-H and MSI-H cohorts, we identified more (a 7.4-fold increase) somatic non-synonymous variations in MLH1 and MSH2 in MSI-H than in non-MSI-H colorectal cancers. A high number of mutated genes in some patients in the non-MSI-H group, shown in FIG. 3, Panel A could correspond to chromosomal instability (CIN) pathway as a distinct form of genomic instability promoting CRC. Furthermore, enrichment of $POL_E$ and EXO1 mutations were detected in 12/33 (36%) non-MSI-H patients with at least 1000 mutations. $POL_E$ mutations in the absence of MMR-deficiency could lead to a hypermutable phenotype in CRC and do not directly demonstrate microsatellite instability. All the COSMIC variants analyzed came from samples tagged as positive "genome-wide screen" indicating whole exome sequencing. However, the low number of mutations in patients with less than 10 mutated genes in the non-MSI-H group can be either because of low-quality genome-wide exome sequencing to detect somatic mutations or because possibly only selected genes were sequenced such as APC, KRAS, and TP53 in some tumors (see, FIG. 3, Panel A).

Deregulation of RTK-RAS, WNT, PI3K, TGF-β and p53 signaling pathways in CRC has been reported in the Cancer Genome Atlas Network (TCGA) study. To further identify MSI effects on mutation frequency of altered pathways in CRC, we compared the non-synonymous mutation frequency in the MSI-H versus non-MSI-H group. In this analysis, we identified APC, KRAS, NRAS and p53 to be mutated in both MSI-H and non-MSI-H CRC samples with no statistically significant difference: APC (88.11% vs. 71.39%), KRAS (42.57% vs. 39.62%), p53 (62.37% vs. 58.29%) and NRAS (8.92% vs. 5.78%) (see, FIG. 3, Panel B).

Figure 3:
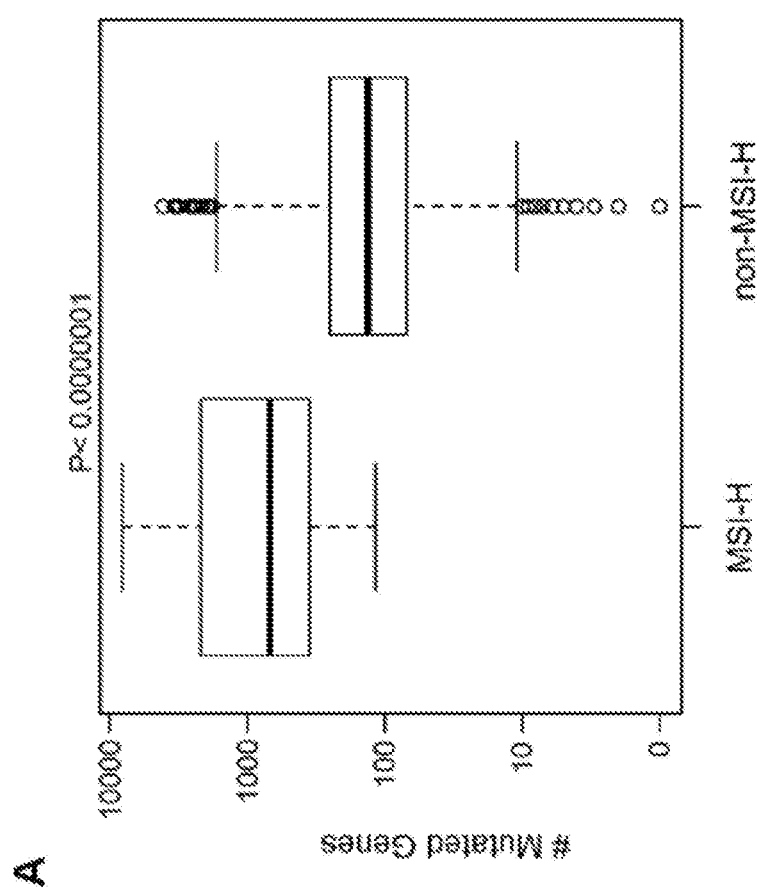
FIG. 3 (Panels A, B, and C): The BRCA2 gene is among the most highly mutated genes with a higher mean number of mutations per tumor in MSI-H CRCs. (Panel A) Difference in number of mutated genes in CRC patients with MSI-H and non-MSI-H are plotted in box-plot (mutation counts are $\log_{10}$ scaled). (Panel B) Genes with different mutation frequencies among the MSI-H and non-MSI-H groups are shown with respect to matters of significance. (Panel C) The columns represent the mean of the number of mutations in the gene, across both MSI-H and non-MSI-H samples. The distribution of mutation counts between MSI-H and non-MSI-H samples were compared by Wilcoxon rank sum tests. Fisher exact test was applied to compare the categorical variables.
Figure 3:
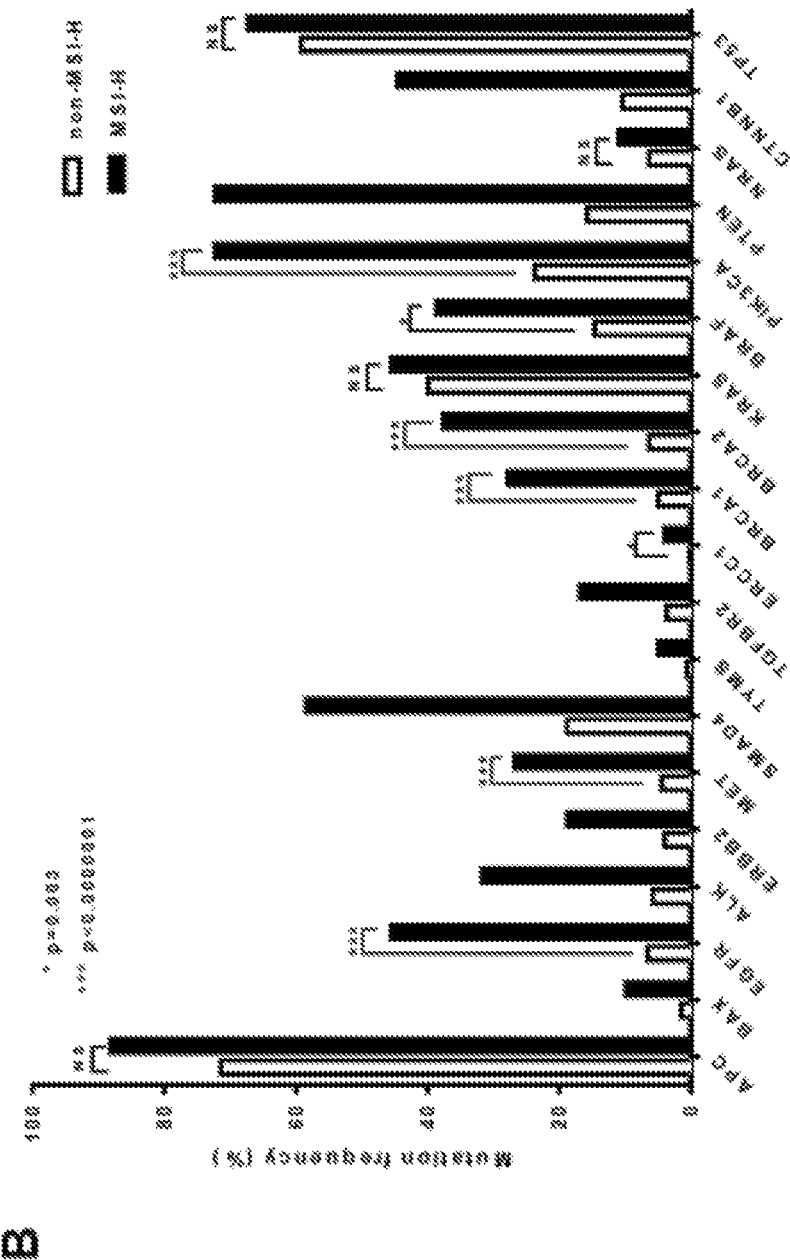
Figure 3:
Figure 9:
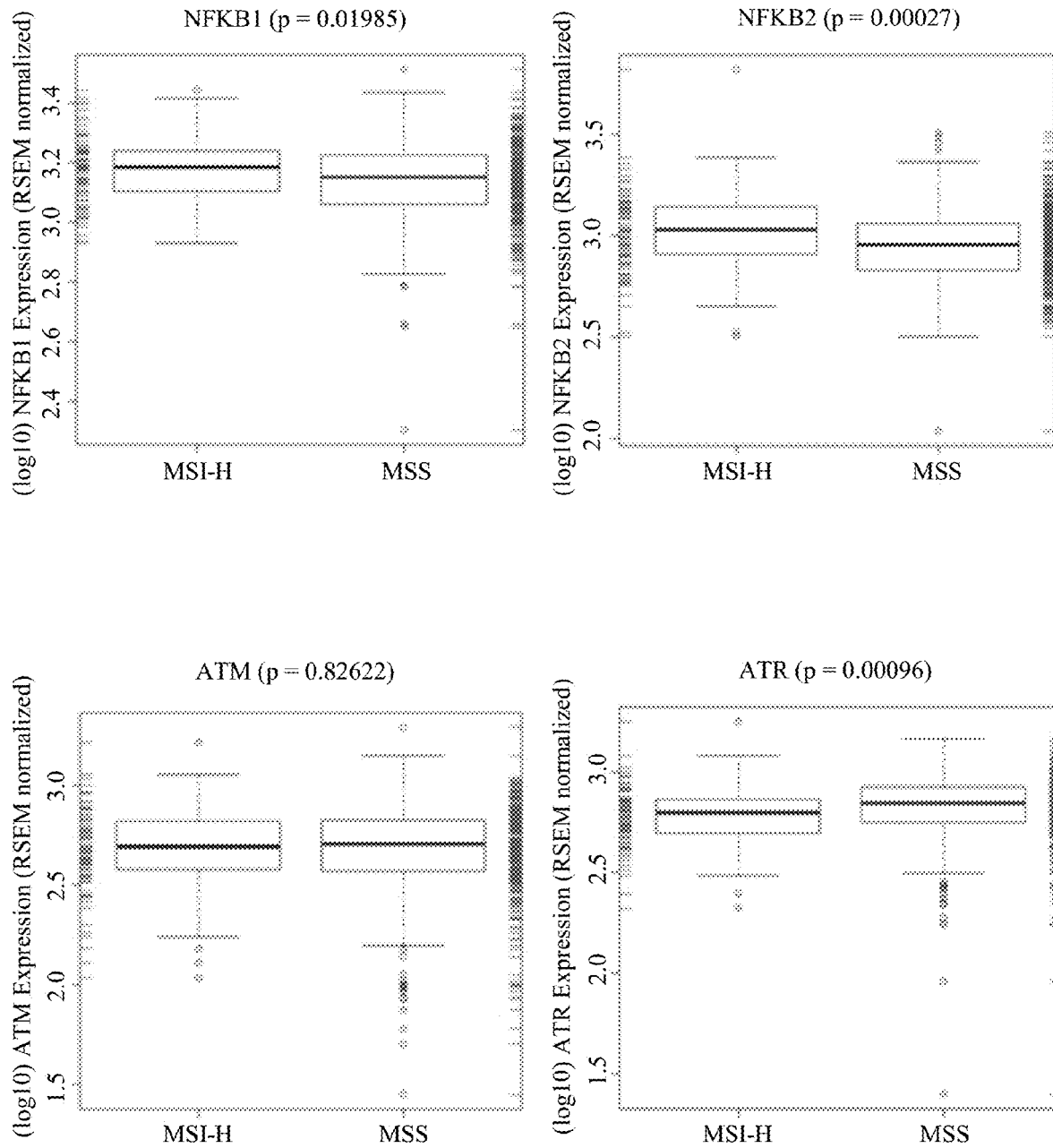
FIG. 9: Association between microsatellite instability and mRNA expression of NFKB1/2, ATM/ATR, CHEK1/2, SMAD4, EGFR, CD274, SPATA2, CTNNB1, AKT1, APC, KRAS, BRCA1/2, TP53, $POL_E$ in CRC patients.
Figure 9:
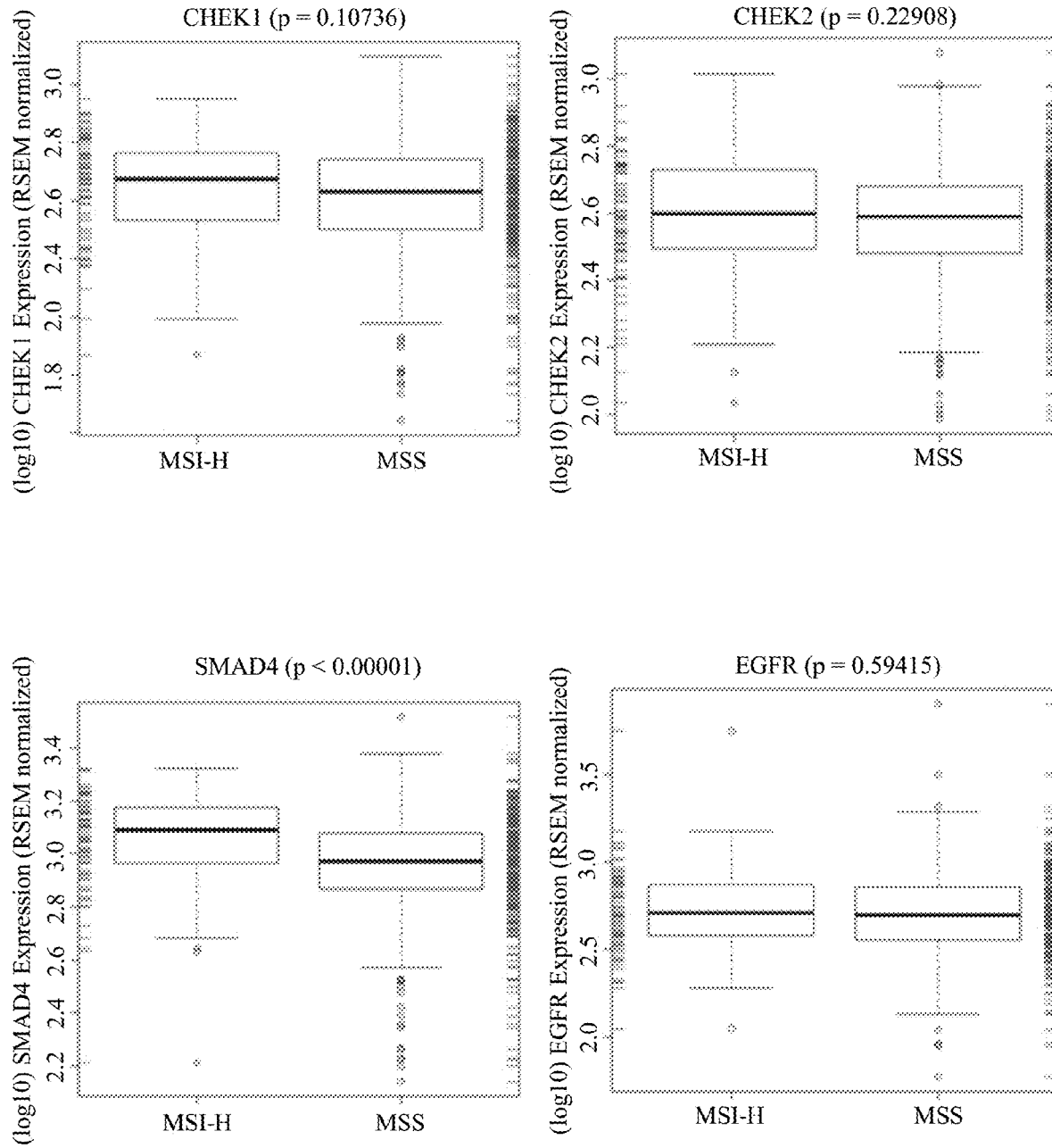
Figure 9:
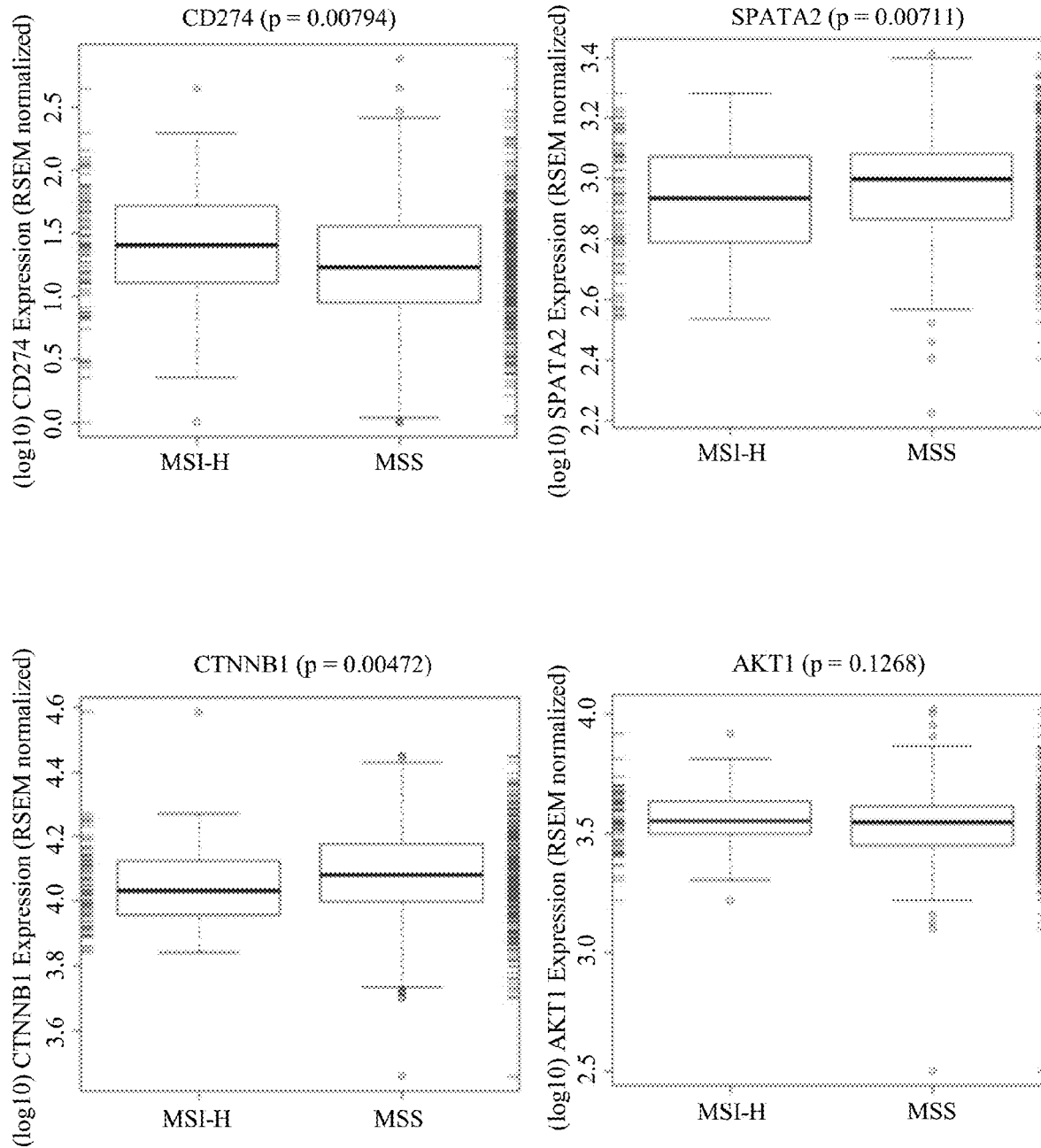
Figure 9:
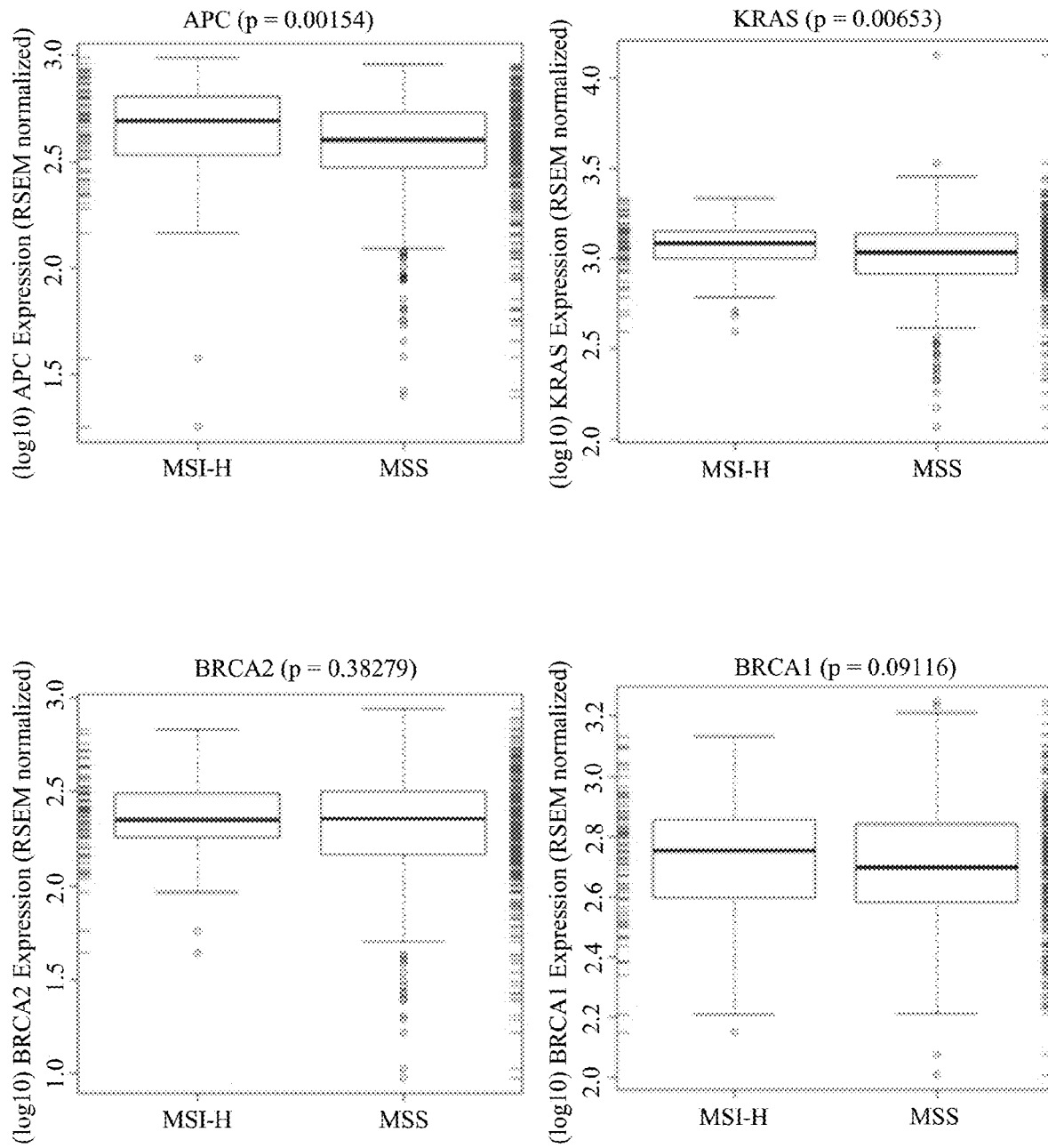
Figure 9:
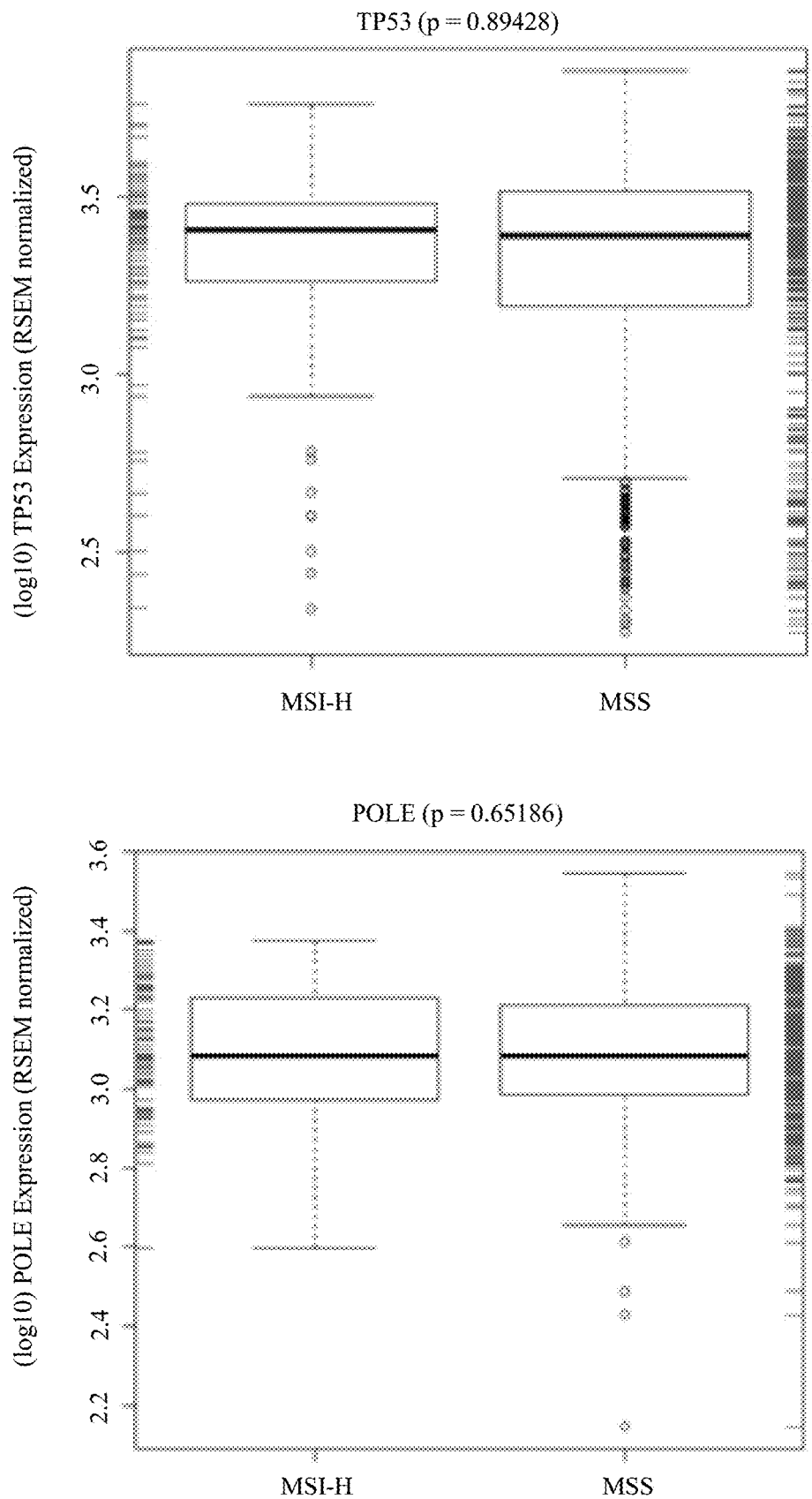

Despite the significantly higher level of APC transcript in MSI-H, CRC subtypes were frequently mutated for APC with a non-significant difference (see, FIG. 3, Panel B, and FIG. 9). Alterations in the p53 pathway were previously found in 59% of non-hypermutated cases, similar to our initial Caris cohort (63%) and the COSMIC cohort (67%). However, our observation in the COSMIC cohort is indicative of a nonsignificant difference in TP53 mutated cases among CRC MSI-H or non-MSI-H subtypes (see, FIG. 3, Panel B). Both MSI-H and non-MSI-H groups appear to express similar levels of TP53 mRNA (see, FIG. 9). Our mutation analysis displays non-MSI-H patients as having a higher frequency of damaging mutations in p53 hotspots at 32% including p.R248, p.G245, p.G244, p.C238, p.M237, p.S215, p.R213, p.Y205, p.R196, p.I195, p.L194, and p.R175H, compared to MSI-H patients at 4%. The data highlights the correlation of p53 mutation and advanced stage of colorectal cancer and the reverse association with MSI (Bond et al., Int'l J. Cancer, 2012, 130, 1567-76).

We observed significant enrichment of mutations in cancer-related genes involved in PI3K and TGFβ3 signaling pathways as well as BRCA genes in MSI-H tumors (see, FIG. 3, Panel B). We note that these mutated genes (PI3K, TGFβ3 and BRCA) have the same level of transcript expression in both MSI-H and non-MSI-H CRC cohorts. CRC patients with BRCA2 mutations are significantly more common in the MSI-H than in the non-MSI-H cohort (37.6% vs 6.3%, p<0.0000001), and the same trend for BRCA1 mutations (27.7% vs 4.9%, p<0.0000001) (see, FIG. 3, Panel B). Although KRAS and NRAS are mutated with a high frequency in both MSI-H and non-MSI-H groups, BRAF is more frequently mutated in MSI-H than in non-MSI-H CRCs (32.67% vs 13.10%; p=0.001) (see, FIG. 3, Panel B), consistent with the known association between MSI-H CRCs with BRAF mutations.

Figure 10:
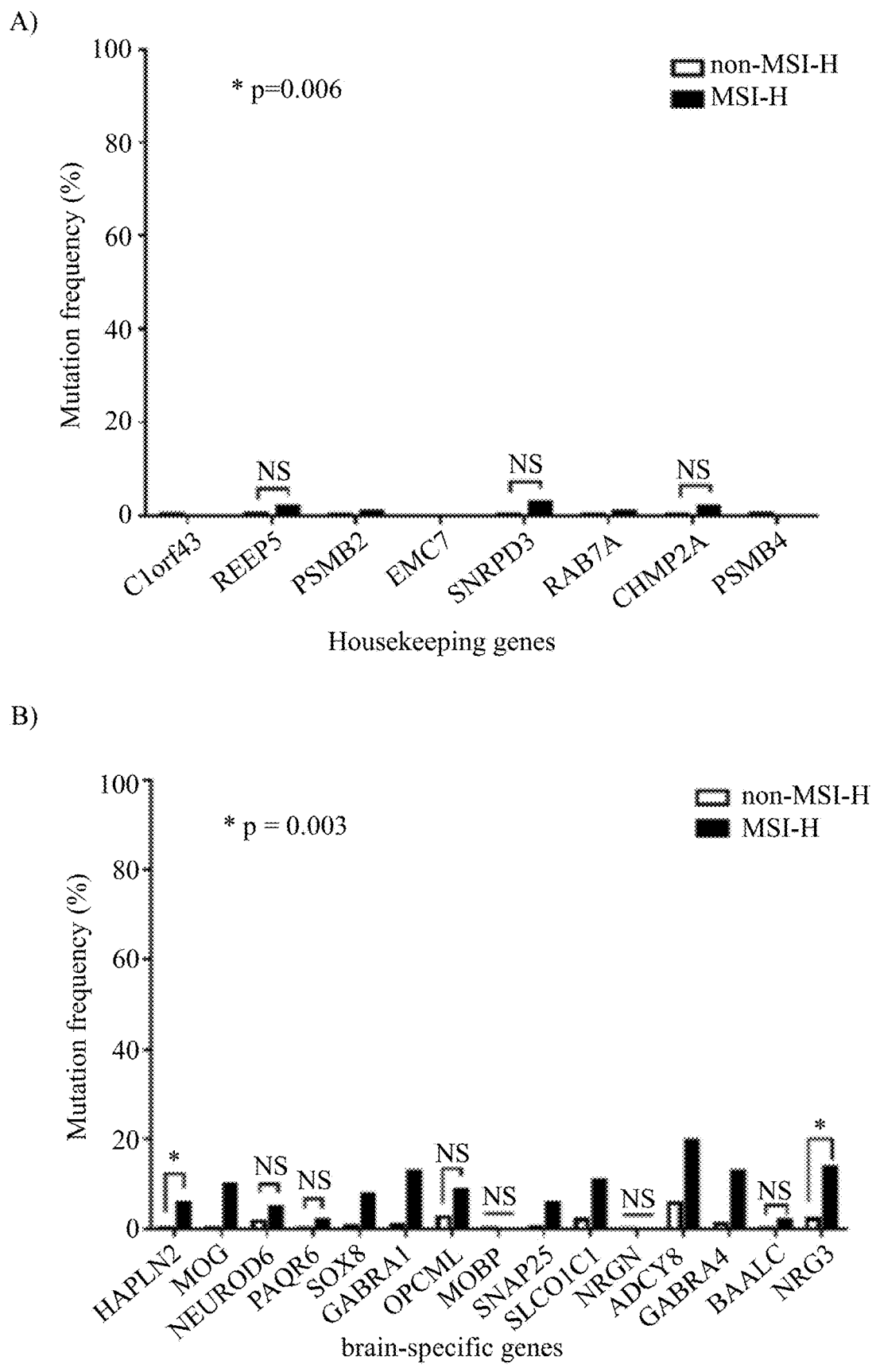
FIG. 10 (Panels A and B): Low frequency of mutations is seen in either randomly picked housekeeping or brain-specific genes. (Panels A and B) Mutation frequencies in MSI-H and non-MSI-H groups are shown with p-values from Fisher's exact tests.

By contrast, we could not detect a significant difference in mutation frequency among randomly picked housekeeping genes in both the MSI-H and non-MSI-H cohorts (see, FIG. 10). Brain-specific genes are less frequently mutated in both groups compared to the highly mutated list of genes. However, some brain-specific genes such as NGR3 and HAPLN2 are highly mutated in the MSI-H group (see, FIG. 10).

A diverse number of mutations was observed in individual CRC patients in each subtype. The distribution of the number of mutations in each gene among MSI-H and non-MSI-H samples with at least one mutation in the particular gene was examined (see, FIG. 3, Panel C). The mean number of mutations in BRCA2 was determined to be significantly higher in the MSI-H than the non-MSI-H CRCs (2.3 vs. 1.1, p<0.0001), suggesting that each CRC patient with MSI has a higher number of BRCA2 mutations than the patients in the non-MSI-H subtype (see, FIG. 3, Panel C). Although CRC patients in both subtypes have a similar mutation frequency of APC and TP53 in the COSMIC dataset, MSI-H CRCs were observed to harbor more APC and TP53 mutations per patient sample as compared to patients in the non-MSI-H cohort (see, FIG. 3, Panel C).

Example 5: BRCA2 Mutations are Distinct Between Non-MSI-H Versus MSI-H CRCs

Figure 11:
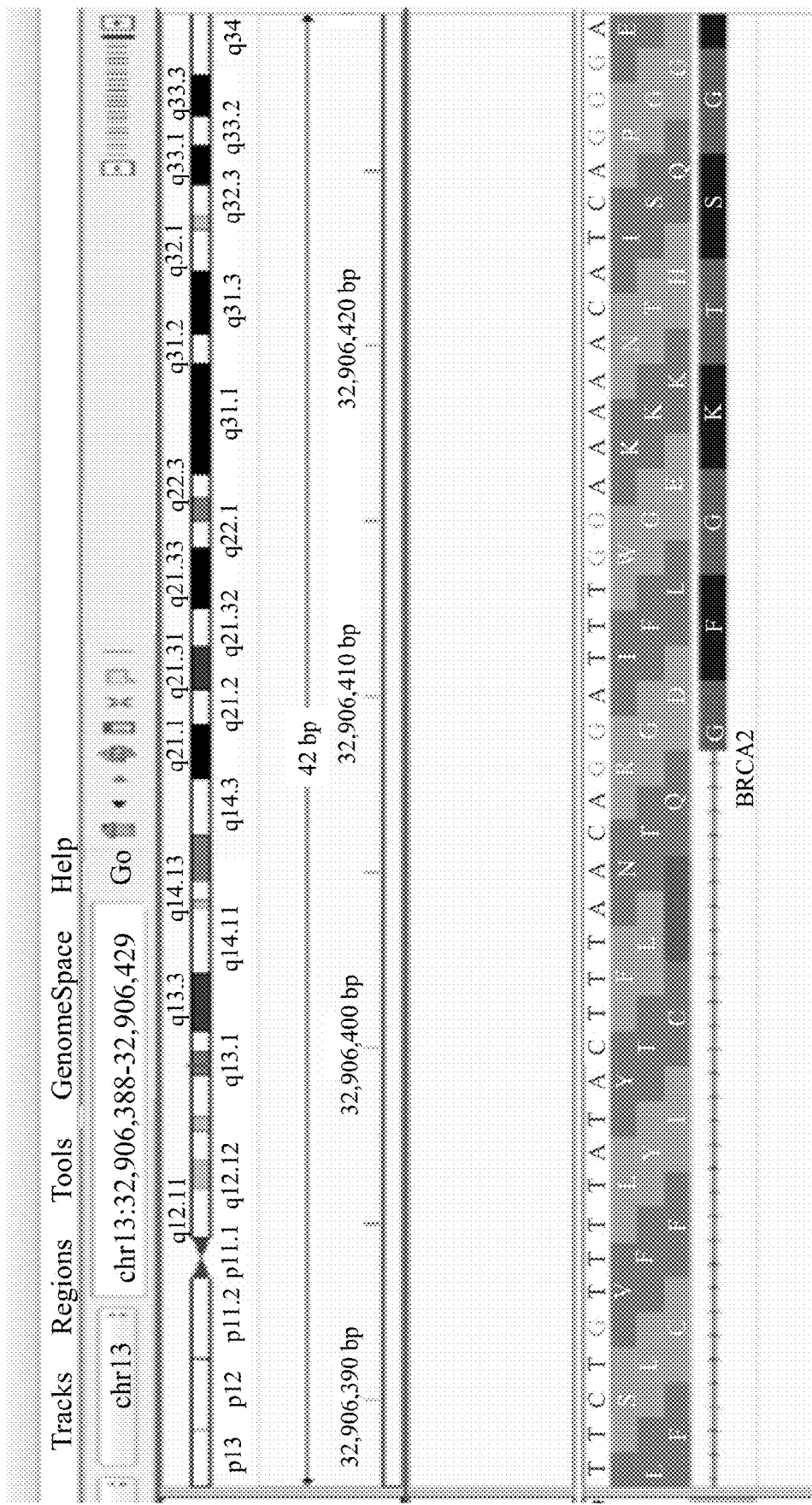
FIG. 11: One of the BRCA2 alterations was detected in splicing site. The red marked site is outside of the coding zone, considered the splicing site. Graphic representation of the specific site visualized with Integrative Genomics Viewer (IGV) software. SEQ ID NO: 4 is shown on top in color; SEQ ID NO: 5 is shown under SEQ ID NO: 4; SEQ ID NO: 6 is shown under SEQ ID NO: 5; SEQ ID NO: 7 is shown to the left of the splicing site; SEQ ID NO: 8 is shown to the right of the splicing site; and SEQ ID NO: 9 is shown at the bottom.

We investigated BRCA1/2 mutations in the MSI-H and the non-MSI-H CRC patient sample groups to decipher the statistical, domain distributional, and functional difference in BRCA mutations of each group. Among 101 MSI-H patients, 46 CRC patients had 88 (75 unique) somatic BRCA2 mutations including 9 frameshift/nonsense (truncating the protein), 56 missense (dysfunctional protein), 9 silent mutations along with one mutation in the splicing site (Table 1, FIG. 11). By contrast, only 58 CRC patients were found to hold 65 (58 unique) somatic BRCA2 mutations among the 916 non-MSI-H patient CRC samples.

Figure 4:
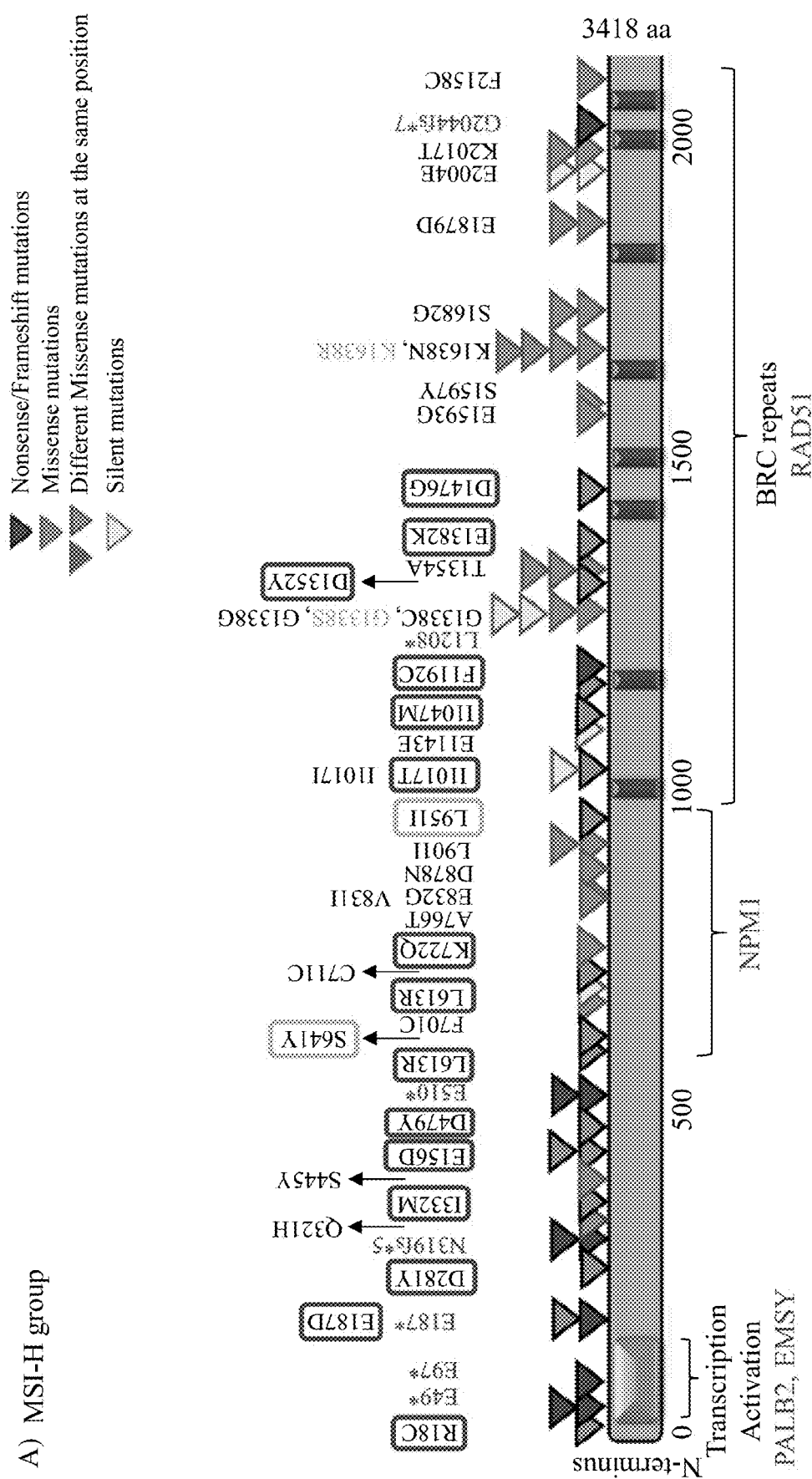
FIG. 4 (Panels A and B): BRCA2 protein domain structure annotated with somatic alterations in MSI-H vs. non-MSI-H CRCs and coding microsatellites. (Panel A) BRCA2 mutations in MSI-H patient samples vs. non-MSI-H samples. Functional domains and interaction partner proteins are annotated in black and green, respectively. Truncating variants including nonsense and frameshift mutations are shown in red. Missense mutations are denoted in blue as well as brown in the same spot. Variants predicted by PolyPhen-2 (world wide web at "genetics.bwh.harvard.edu/pph2/") to be damaging are denoted in black-outlined triangle as well as red/orange rectangle. Red rectangles are representative of damaging mutations with high probability (>90%) and orange rectangles outline the mutations with possibility (>50%). Synonymous variants are shown in white triangles. (Panel B) BRCA2 and mutations in coding repetitive sequences in both groups.
Figure 4:
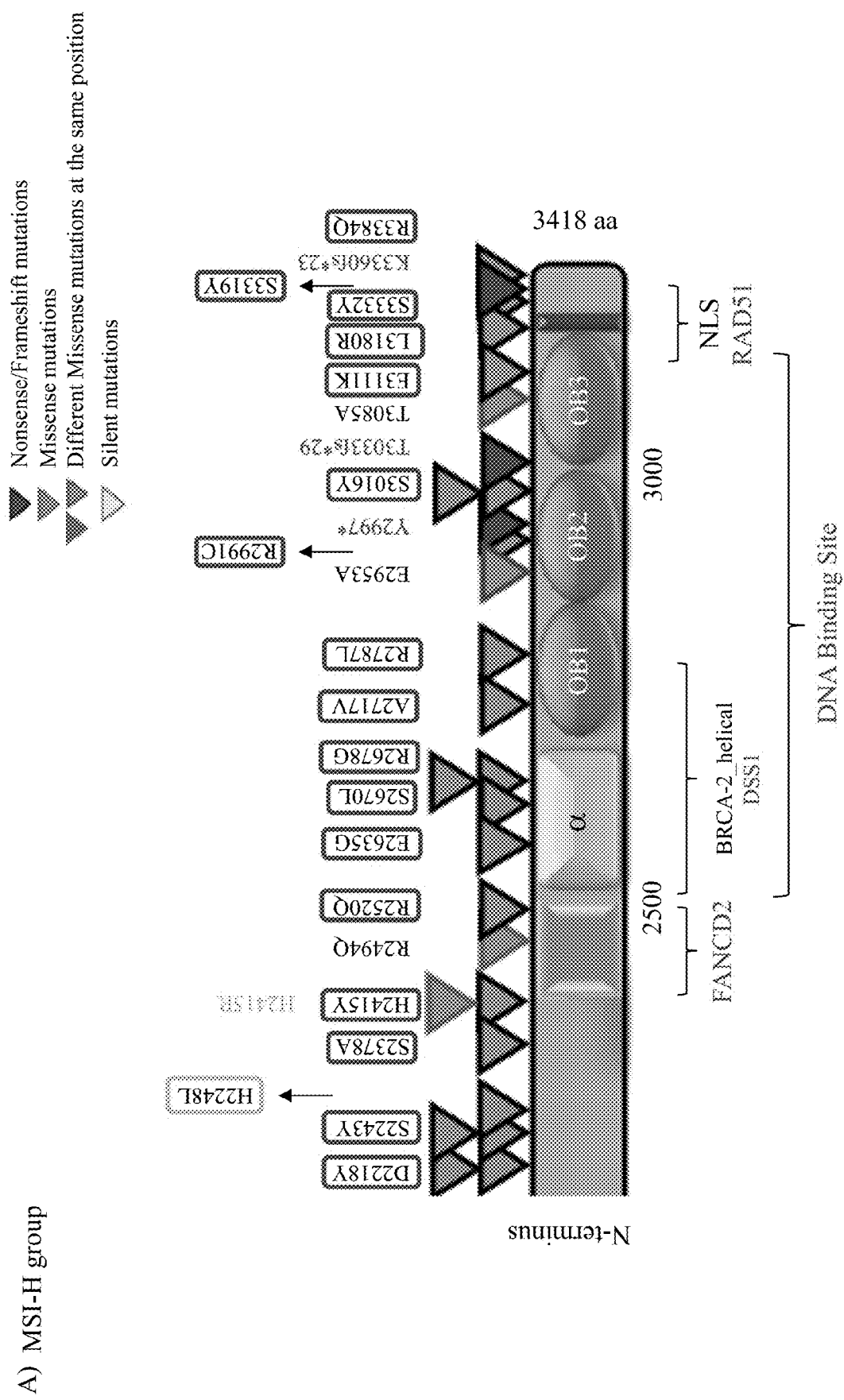
Figure 4:
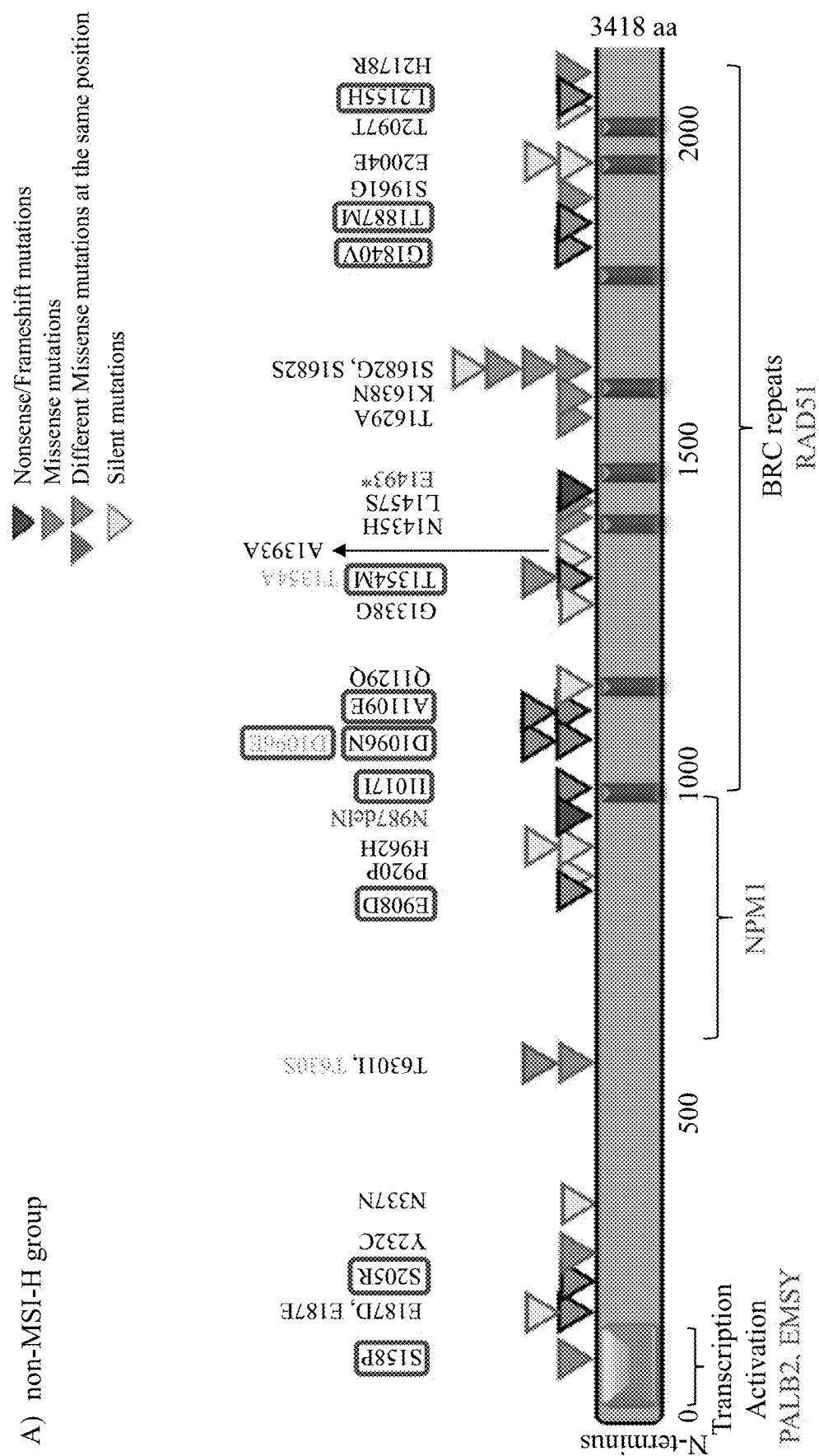
Figure 4:
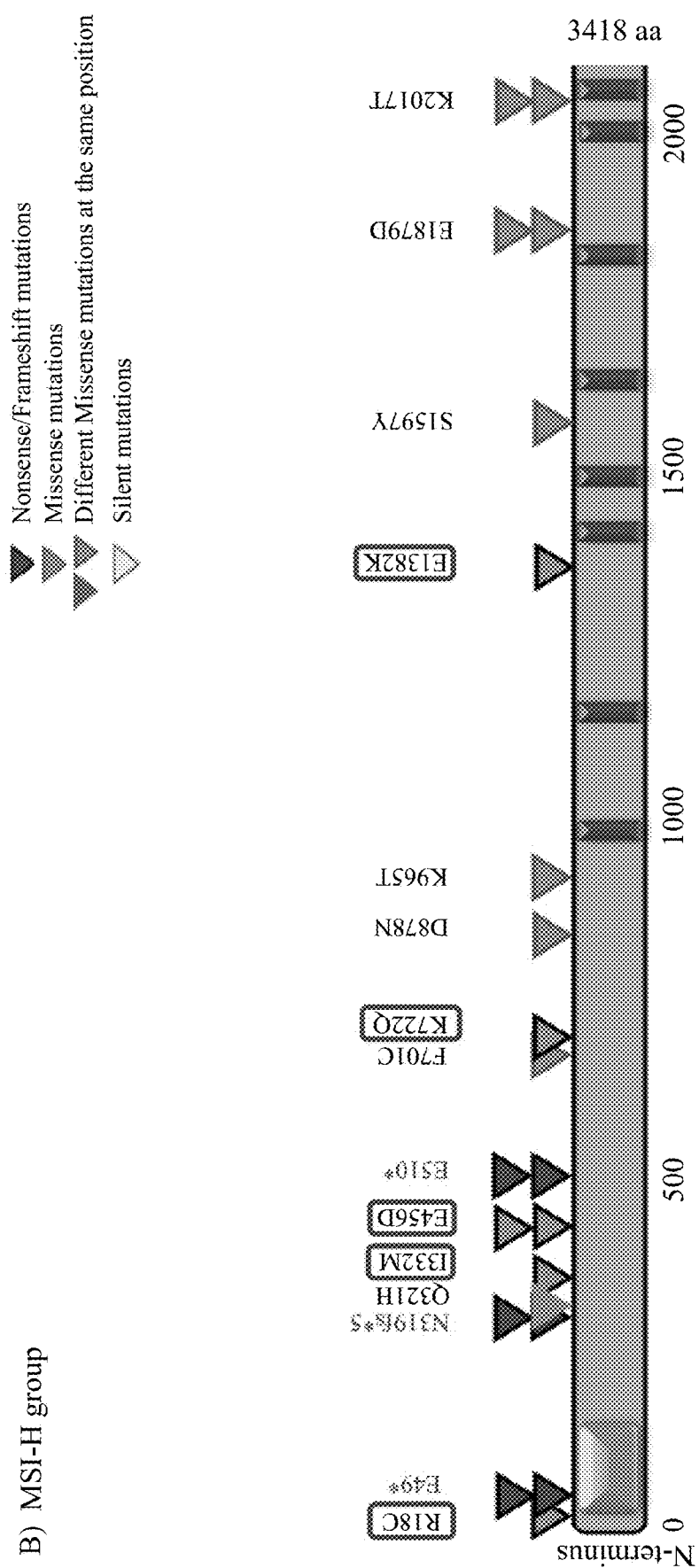
Figure 4:
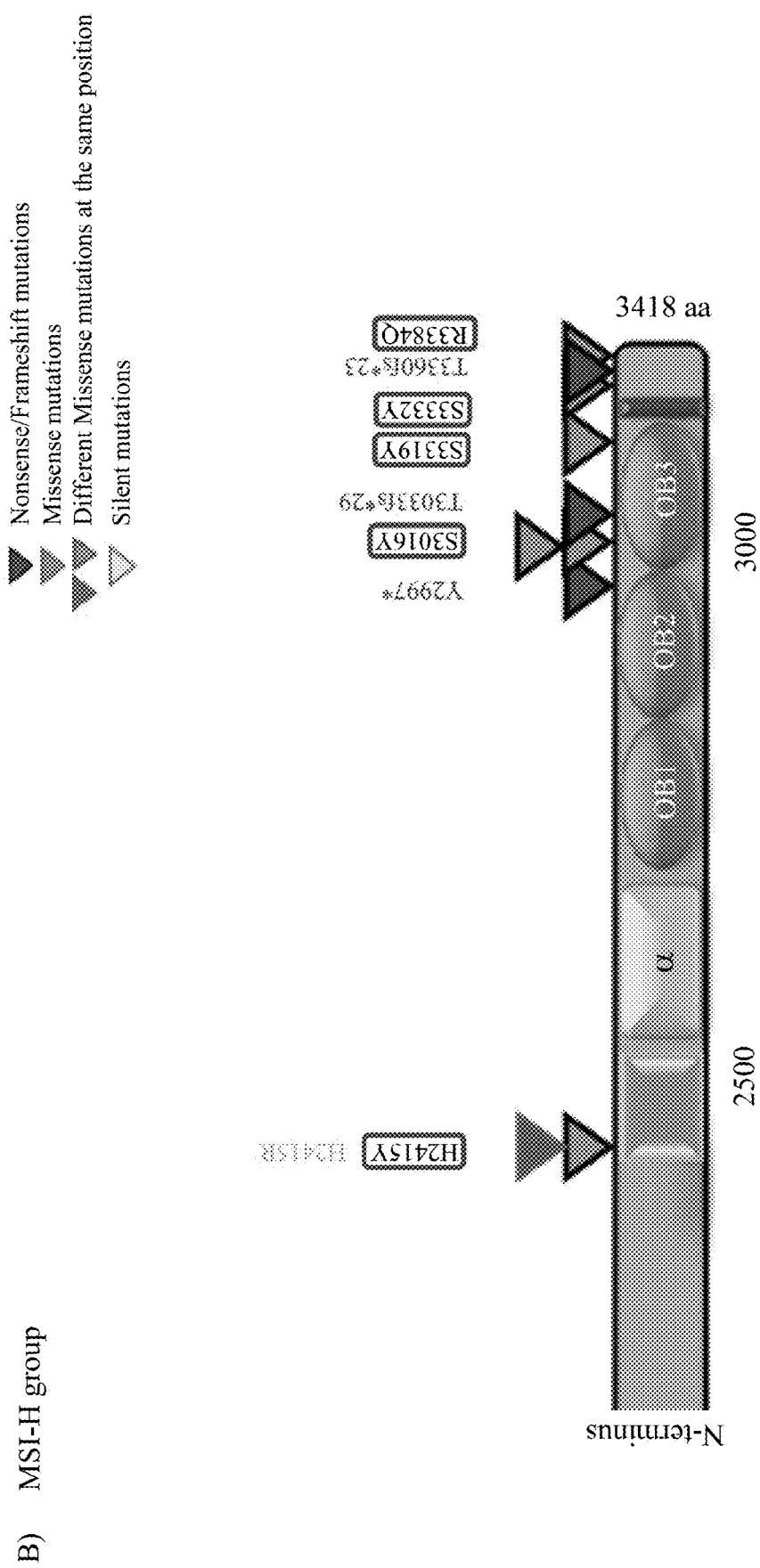
Figure 4:
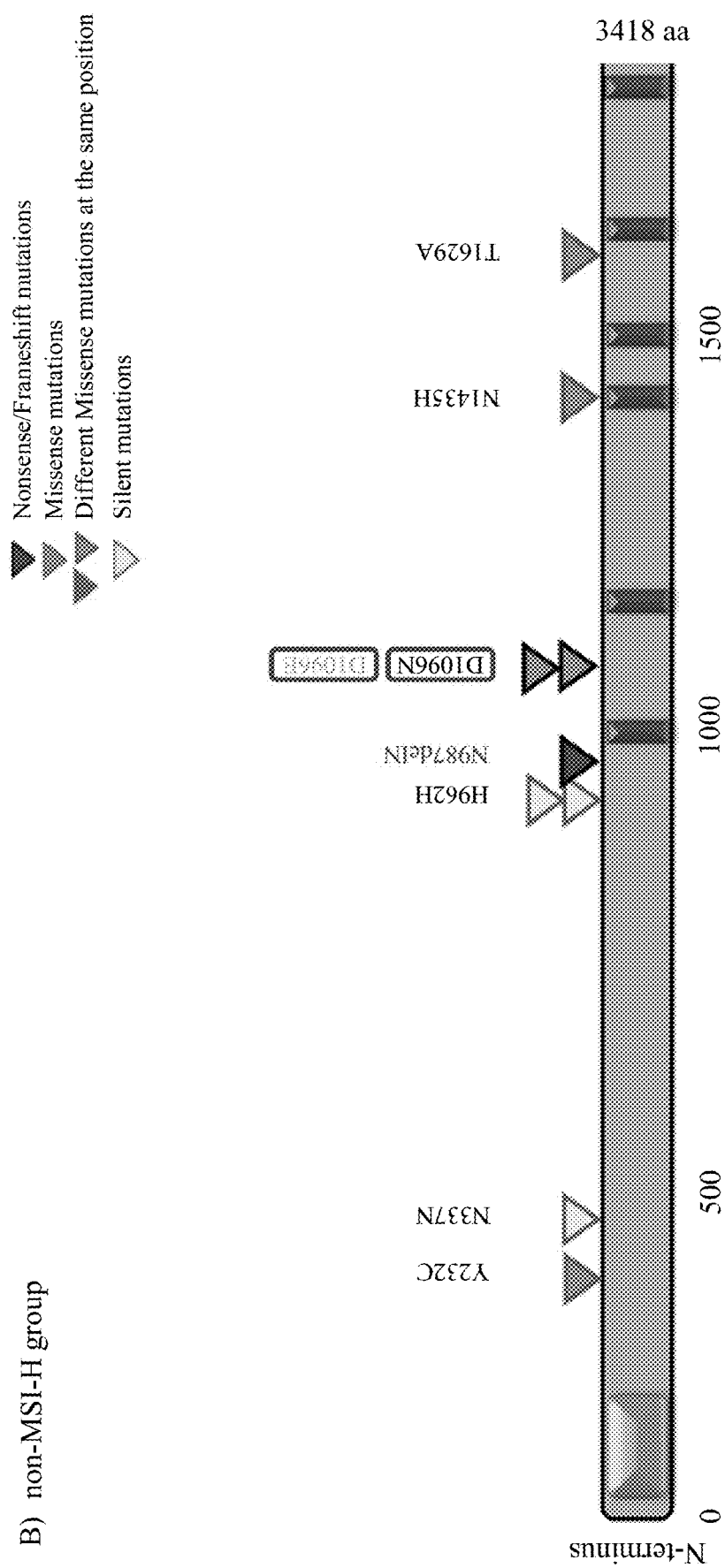
Figure 4:
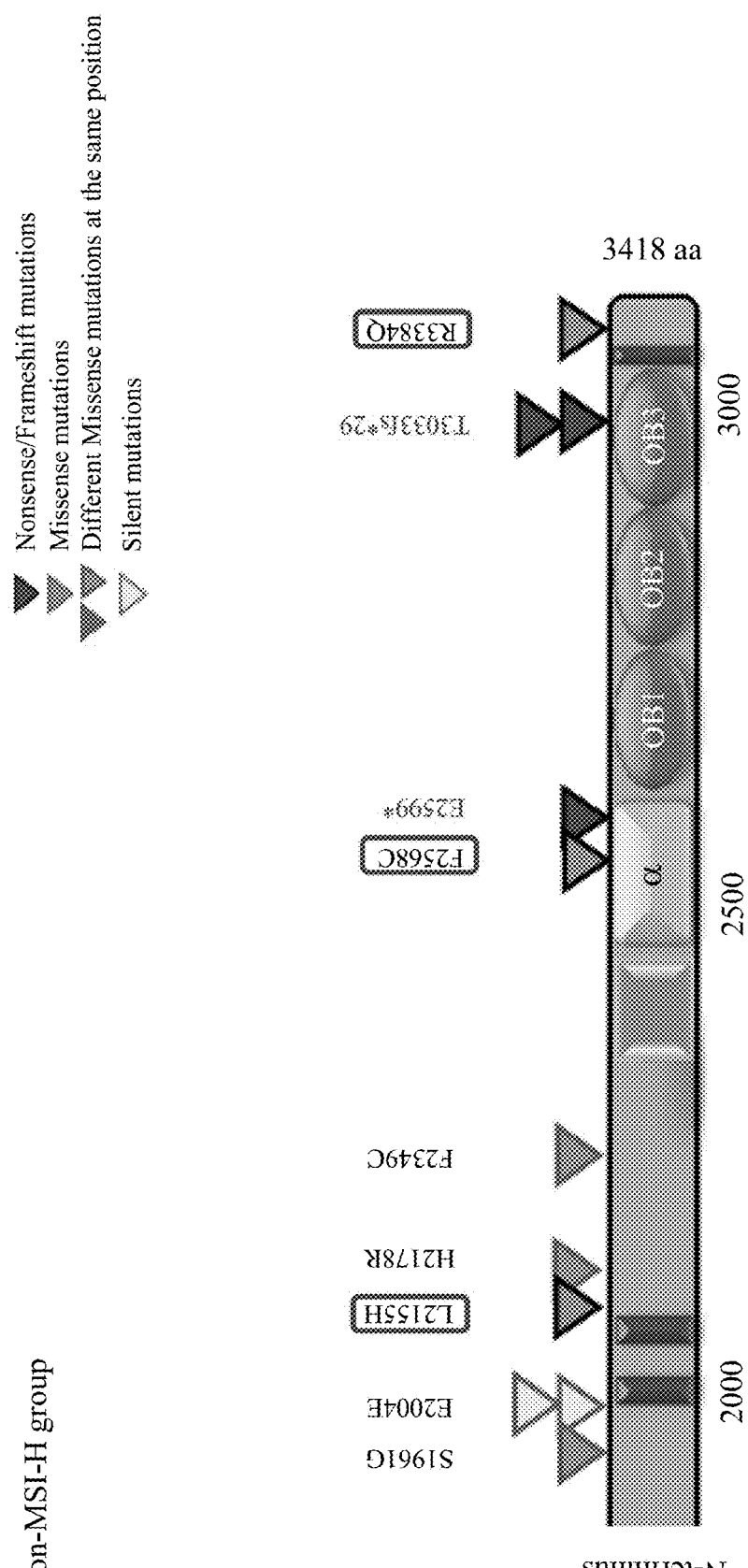

Somatic mutations in BRCA2 derived from the COSMIC dataset v73 were mapped on the BRCA2 protein structure with known functional domains (see, FIG. 4, Panels A and B). The majority of somatic mutations were missense variants with an unknown functional effect. Using the protein structural predictor, PolyPhen-2, we assigned missense mutations as damaging or neutral. High score of Polyphen-2 is indicative of missense mutations leading to prevention of partial or total misfolding of the corresponded domains in the protein. Of the 56 BRCA2 missense mutations detected in the MSI-H tumors, 39 (70) were predicted to be damaging, disrupting protein structure and protein-protein interaction interference (see, FIG. 3, Panels A, B, and C, and Table 2). We did not detect a significant difference in BRCA1 somatic mutations between the MSI-H vs the non-MSI-H CRC groups (see, Table 1). Therefore, our study focused more on BRCA2 somatic mutations in MSI-H CRCs.

TABLE 2

The consensus prediction results of BRCA2 mutations in MSI648 H patients

| Mutation CDS | Mutation AA | Breast/ovarian/ pancreatic/uterine cancer germline | Consensus | EXAC frequency | Site subtype | Microsatellite target |
|---|---|---|---|---|---|---|
| c.10151G > A | p.R3384Q | BREAST | Deleterious | N/A | rectum | X |
| c.1334C > A | p.S445Y | N | Neutral | N/A | colon | |
| c.1368G > T | p.E456D | N | Deleterious | N/A | rectum | X |
| c.1435G > T | p.D479Y | PANCREATIC | Deleterious | N/A | colon | |
| c.1838T > G | p.L613R | N | Deleterious | <1/10.000 | colon | |
| c.1922C > A | p.S641Y | N | Deleterious | N/A | caecum | |
| c.2102T > G | p.F701C | N | Deleterious | N/A | colon | X |
| c.2164A > C | p.K722Q | N | Deleterious | N/A | rectum | X |
| c.2296G > A | p.A766T | N | Neutral | N/A | colon | |
| c.2491G > A | p.V831I | BREAST | Neutral | N/A | colon | |
| c.2495A > G | p.E832G | N | Neutral | N/A | colon | |
| c.2632G > A | p.D878N | N | Neutral | <1/10.000 | caecum | X |
| c.2701C > A | p.L901I | N | Neutral | N/A | colon | |
| c.2851C > A | p.L951I | N | Neutral | N/A | colon | |
| c.2867A > C | p.K956T | N | Neutral | N/A | colon | |
| c.3050T > C | p.I1017T | SAME POSITION | Deleterious | N/A | colon | |
| c.3141T > G | p.I1047M | N | Deleterious | N/A | rectum | |
| c.3575T > G | p.F1192C | BREAST | Deleterious | 1/10.000-0.001 | colon | |
| c.4012G > A | p.G1338S | SAME POSITION | Deleterious | N/A | caecum | |
| c.4012G > T | p.G1338C | SAME POSITION | Deleterious | N/A | colon | |
| c.4054G > T | p.D1352Y | BREAST | Deleterious | N/A | colon | |
| c.4144G > A | p.E1382K | SAME POSITION | Deleterious | N/A | colon | X |
| c.4427A > G | p.D1476G | N | Deleterious | Singleton | colon | |
| c.4778A > G | p.E1593G | N | Deleterious | N/A | colon | |
| c.4790C > A | p.S1597Y | N | Neutral | N/A | rectum | X |
| c.4913A > G | p.K1638R | OVARIAN | Neutral | N/A | caecum | |
| c.4914A > T | p.K1638N | N | Deleterious | N/A | caecum | |
| c.52C > T | p.R18C | N | Deleterious | N/A | colon | X |
| c.561G > T | p.E187D | SAME POSITION | Deleterious | Singleton | caecum | |
| c.5637G > T | p.E1879D | SAME POSITION | Deleterious | N/A | rectum | X |
| c.6050A > C | p.K2017T | N | Deleterious | N/A | rectum | X |
| c.6473T > G | p.F2158C | N | Neutral | N/A | caecum | |
| c.6652G > T | p.D2218Y | N | Deleterious | N/A | rectum | |
| c.6728C > A | p.S2243Y | N | Deleterious | N/A | rectum | |
| c.6743A > T | p.H2248L | N | Neutral | N/A | NS | |
| c.7132T > G | p.S2378A | SAME POSITION | Deleterious | N/A | rectum | |
| c.7243C > T | p.H2415Y | N | Deleterious | N/A | colon | X |
| c.7244A > G | p.H2415R | N | Neutral | Singleton | colon | X |
| c.7481G > A | p.R2494Q | BREAST | Deleterious | N/A | rectum | |
| c.7559G > A | p.R2520Q | BREAST | Deleterious | <1/10.000 | caecum | |
| c.7904A > G | p.E2635G | N | Deleterious | N/A | colon | |
| c.8009C > T | p.S2670L | BREAST | Deleterious | N/A | rectum | |
| c.8032A > G | p.R2678G | N | Deleterious | N/A | colon | |
| c.8150C > T | p.A2717V | SAME POSITION | Deleterious | N/A | colon | |
| c.8360G > T | p.R2787L | SAME POSITION | Deleterious | N/A | caecum | |
| c.841G > T | p.D281Y | SAME POSITION | Deleterious | N/A | colon | |
| c.8858A > C | p.E2953A | N | Neutral | N/A | caecum | |
| c.8971C > T | p.R2991C | SAME POSITION | Deleterious | Singleton | colon | |
| c.9047C > A | p.S3016Y | N | Deleterious | N/A | rectum | |
| c.9253A > G | p.T3085A | SAME POSITION | Neutral | N/A | caecum | X |
| c.9331G > A | p.E3111K | N | Deleterious | N/A | colon | |
| c.9539T > G | p.L3180R | SAME POSITION | Deleterious | N/A | rectum | |
| c.963A > C | p.Q321H | SAME POSITION | Neutral | N/A | rectum | X |
| c.9956C > A | p.S3319Y | N | Deleterious | N/A | colon | X |
| c.996T > G | p.I332M | N | Neutral | N/A | caecum | X |
| c.9995C > A | p.S3332Y | N | Deleterious | N/A | colon | X |

We show that MSI-H CRCs display a distinct pattern of BRCA2 mutations as reflected in the frequency, diversity and position of the mutations by comparison to the non-MSI-H CRCs. Significantly more BRCA2 mutations were predicted to be damaging in the MSI-H CRCs as compared to the non-MSI-H CRCs (64% vs 43%, p=0.0045) (see, FIG. 4, Panels A and B). More frameshift and/or nonsense point mutations were observed to be distributed in the N-terminal, BRC repeats and C-terminal regions of BRCA2 in the MSI-H group (see, FIG. 4, Panels A and B). These could generate a truncated protein that may be subject to protease-mediated degradation and lead to deficient HR in the cell. Most of the observed mutations accumulated in the C-terminal portion of BRCA2 suggesting this area may have an important function, through interaction with DSS1 and RAD51 to facilitate HR (30). Mutations in these C-terminal domains with high mutational density could be tumor-specific or due to an environmental influence. Only few of the BRCA2 mutations in CRCs have been reported in breast/ovarian cancer suggesting that these mutations may be CRC-specific.

Different repetitive sequences (mononucleotides, dinucleotides, and trinucleotides) and their frequency were sought in BRCA2 and they were integrated with corresponding somatic mutations and involved domains. Of 123 distinct BRCA alterations in both CRC groups, 39 variations with a deleterious effect were mapped on coding microsatellites (see, Table 3, FIG. 4, Panel B). Altogether, our data suggests coding microsatellites in BRCA2 are more mutated with a higher potential for damaging mutations in the MSI-H patients than in the non-MSI-H group. This analysis highlights the significance of the underlying genetic signature and impact of deficient MMR on mutations of coding microsatellites in BRCA2.

TABLE 3

Polynucleotide repeats in coding BRCA2 are hotspots for alterations

| | repeats | counts | Mutation involved | Involved Domain |
|---|---|---|---|---|
| Mononucleotide | AAAA | 103 | K2017T, T1629A | Between BRC 7, 8 |
| | AAAAA | 60 | Q321H, K965T, | Interaction with NPM1 |
| | AAAAAA | 13 | **K722Q, K3360fs*23** | |
| | AAAAAAA | 8 | **N319fs*5**, T3085A, | BRCA2DBD_OB3 |
| | AAAAAAAA | 2 | **T3033fs*29** | BRCA2DBD_OB2 |
| | AAAAAAAAA (SEQ ID NO: 1) | 1 | | |
| | TTTT | 52 | I332M, H2415Y, | Interaction with FANCD2 |
| | TTTTT | 16 | H2415R, N337N, | |
| | TTTTTT | 3 | D1096N/E, F2349C, | |
| | TTTTTTTT | 1 | F2568C, Y232C | |
| | TTTTTTTTT (SEQ ID NO: 2) | 1 | | |
| | CCCC | 12 | | |
| | CCCCC | 1 | | |
| | GGGG | 5 | | |
| Dinucleotide | ACAC | 15 | R18C | Interaction with PALB2 |
| | ACACA | 12 | | |
| | CACA | 26 | | |
| | CACAC | 2 | | |
| | CACACA | 3 | | |
| | TCTC | 19 | S3319Y | Around NLS |
| | TCTCT | 10 | S3332Y | Around NLS |
| | TCTCTC | 4 | S1597Y | Interaction with POLH |
| | TCTCTCT | 1 | | |
| | TCTCTCTC | 1 | L2155H | |
| | CTCT | 23 | D878N | Interaction with NPM1 |
| | CTCTC | 1 | | |
| | CTCTCT | 2 | | |
| | AGAG | 29 | | |
| | AGAGA | 19 | E456D, E510* | |
| | AGAGAG | 3 | | |
| | AGAGAGA | 1 | | |
| | GAGA | 26 | E1879D | Between BRC 6, 7 |
| | GAGAG | 4 | | |
| | GAGGAG | 2 | | |
| | GTGT | 13 | | |
| | GTGTG | 5 | | |
| | GTGTGT | 1 | | |
| | TGTG | 25 | | |
| | TGTGT | 10 | | |
| | TGTGTG | 1 | | |

TABLE 3 -continued

Polynucleotide repeats in coding BRCA2 are hotspots for alterations

| | repeats | counts | Mutation involved | Involved Domain |
|---|---|---|---|---|
| | ATAT | 42 | N1435H | Interaction |
| | ATATA | 11 | H962H | with NPM1 |
| | ATATAT | 4 | | |
| | TATA | 22 | S1961G | BRCA2DBD_OB2 |
| | TATAT | 7 | Y2997* | |
| | TATATA | 1 | | |
| | GCGC | 1 | | |
| Trinucleo-tide | AACAAC | 2 | | |
| | AACAACA | 1 | | |
| | AACAACAA | 1 | | |
| | AAGAAG | 3 | E1382K | Interaction |
| | AAGAAGA | 4 | E2599* | with POLH |
| | AAGAAGAA | 3 | | |
| | AATAAT | 7 | N987deIN | Interaction |
| | AATAATA | 2 | | with NPM1 |
| | AATAATAA | 1 | | |
| | ACAACA | 3 | | |
| | ACAACAA | 1 | | |
| | ACGACG | 1 | R3384Q | NLS |
| | ACTACT | 3 | | |
| | AGAAGA | 9 | E2004E | Transcriptional |
| | AGAAGAA | 4 | E49* | activation |
| | AGCAGC | 1 | | |
| | AGCAGCA | 3 | | |
| | AGCAGCAG | 1 | | |
| | AGCAGCAGC | 1 | | |
| | AGGAGG | 2 | | |
| | AGGAGGA | 2 | | |
| | AGTAGT | 1 | | |
| | ATAATA | 1 | | |
| | ATTATT | 6 | | |
| | ATTATTA | 1 | | |
| | CAACAA | 5 | | |
| | CAACAAC | 1 | | |
| | ATGATG | 1 | | |
| | ATGATGA | 3 | | |
| | ATCATC | 3 | | |
| | CACCAC | 2 | | |
| | CACCACC | 1 | | |
| | CAGCAGCA | 1 | | |
| | CATCAT | 1 | | |
| | CATCATC | 1 | | |
| | CATCATCA | 1 | | |
| | CCACCA | 2 | | |
| | CCACCACCAC (SEQ ID NO: 3) | 1 | | |
| | CGCG | 1 | | |
| | CTACTA | 4 | | |
| | CTCCTC | 1 | S3319Y | Around NLS |
| | CTGCTG | 1 | | |

TABLE 3 -continued

Polynucleotide repeats in coding BRCA2 are hotspots for alterations

| repeats | counts | Mutation involved | Involved Domain |
|---|---|---|---|
| CTGCTGC | 1 | | |
| CTTCTT | 1 | | |
| CTTCTTC | 2 | | |
| GAAGAA | 15 | | |
| GAAGAAG | 1 | | |
| GAAGAAGA | 1 | | |
| GAAGAAGAA | 1 | | |
| GATGAT | 1 | | |
| GATGATG | 1 | | |
| GATGATGA | 1 | | |
| GCAGCA | 1 | | |
| GCAGCAG | 1 | | |
| GGAGGA | 2 | | |
| GGAGGAG | 1 | | |
| GGTGGT | 2 | | |
| GTAGTA | 1 | | |
| GTAGTAG | 1 | | |
| GTCGTC | 1 | | |
| GTGGTG | 2 | | |
| GTTGTT | 2 | | |
| TAATAA | 2 | F701C | Interaction with NPM1 |
| TAATAAT | 1 | | |
| TAATAATA | 1 | | |
| TACTAC | 2 | | |
| TACTACT | 1 | | |
| TAGTAG | 1 | | |
| TAGTAGT | 1 | | |
| TATTAT | 1 | | |
| TATTATT | 1 | | |
| TCATCA | 1 | | |
| TCCTCC | 1 | | |
| TCTTCT | 1 | | |
| TGATGA | 5 | | |
| TGATGAT | 1 | | |
| TGCTGC | 1 | | |
| TGGTGG | 2 | | |
| TGTTGT | 1 | | |
| TGTTGTT | 2 | | |
| TTATTA | 3 | F701C | Interaction with NPM1 |
| TTCTTC | 7 | | |
| TTCTTCT | 1 | | |
| TTGTTG | 2 | | |

*Bolded mutations are predicted to be damaging.
** The underlined mutations exist within the underlined domains.

Figure 5:
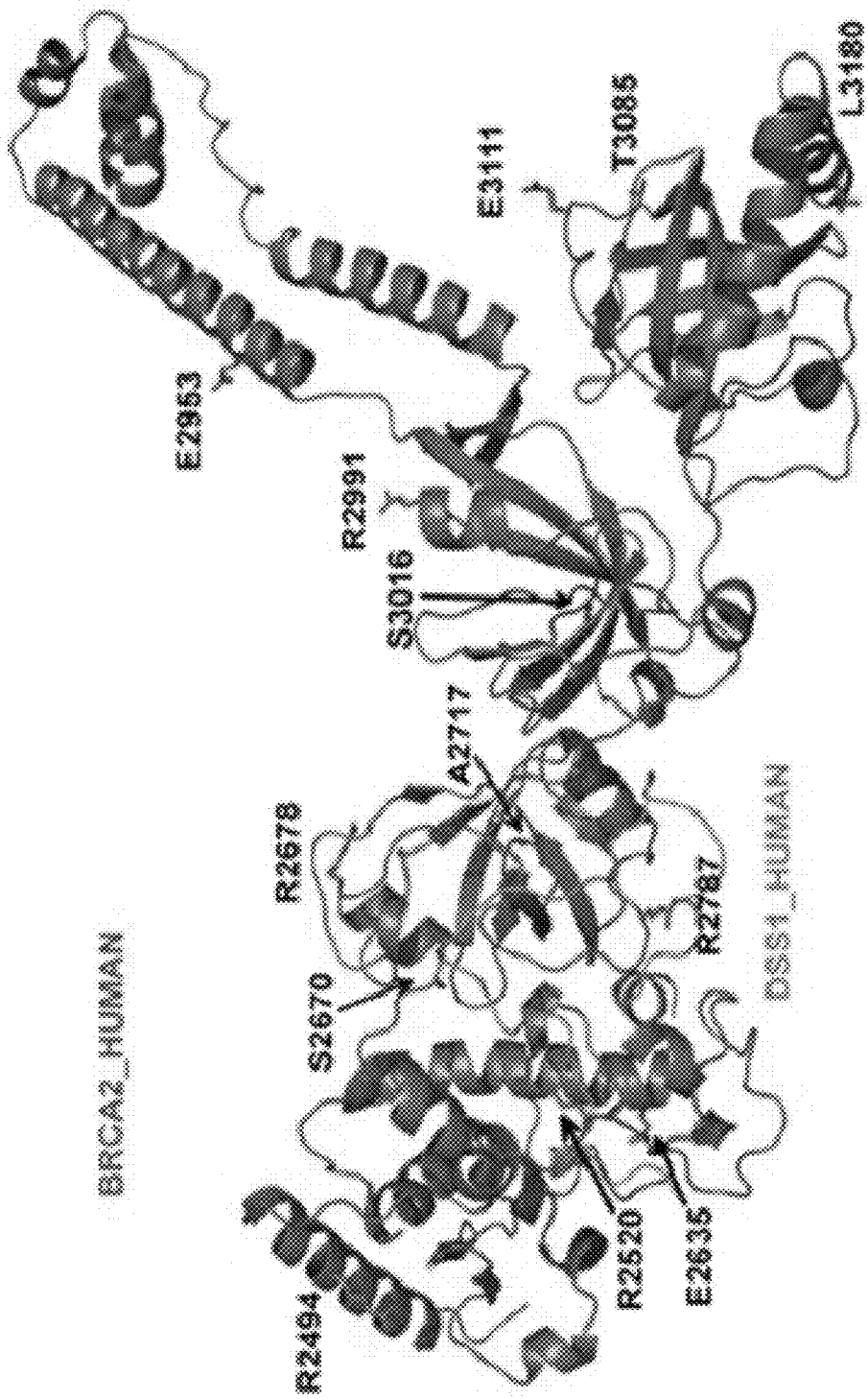
FIG. 5 (Panels A, B, and C): Model depicting the mutations in human BRCA2 that may impact interaction with DSS1. (Panel A) The structure contains 13 mutations which are colored in magenta and shown in sticks. The residues and their sequence numbers are labeled in black. The figure is generated by PyMOL (world wide web at "pymol.org/pymol"). (Panel B) The hydrogen bonds of Arg2520 and Glu14 and Glu18 of DSS1. The hydrogen bond is colored in green and shown in dot lines. The residues are colored in elements, where oxygen atom is colored in red, nitrogen is colored in blue. A hydrophilic pocket of DSS1 is composed of all negative electrically charged residues Glu14, Glu15, Asp16, Asp17 and Glu18. (Panel C) Thr3085 has no side-chain interactions with its neighbor residues (Lys3083, Lys3084, Gly3086 and Leu3087).
Figure 5:
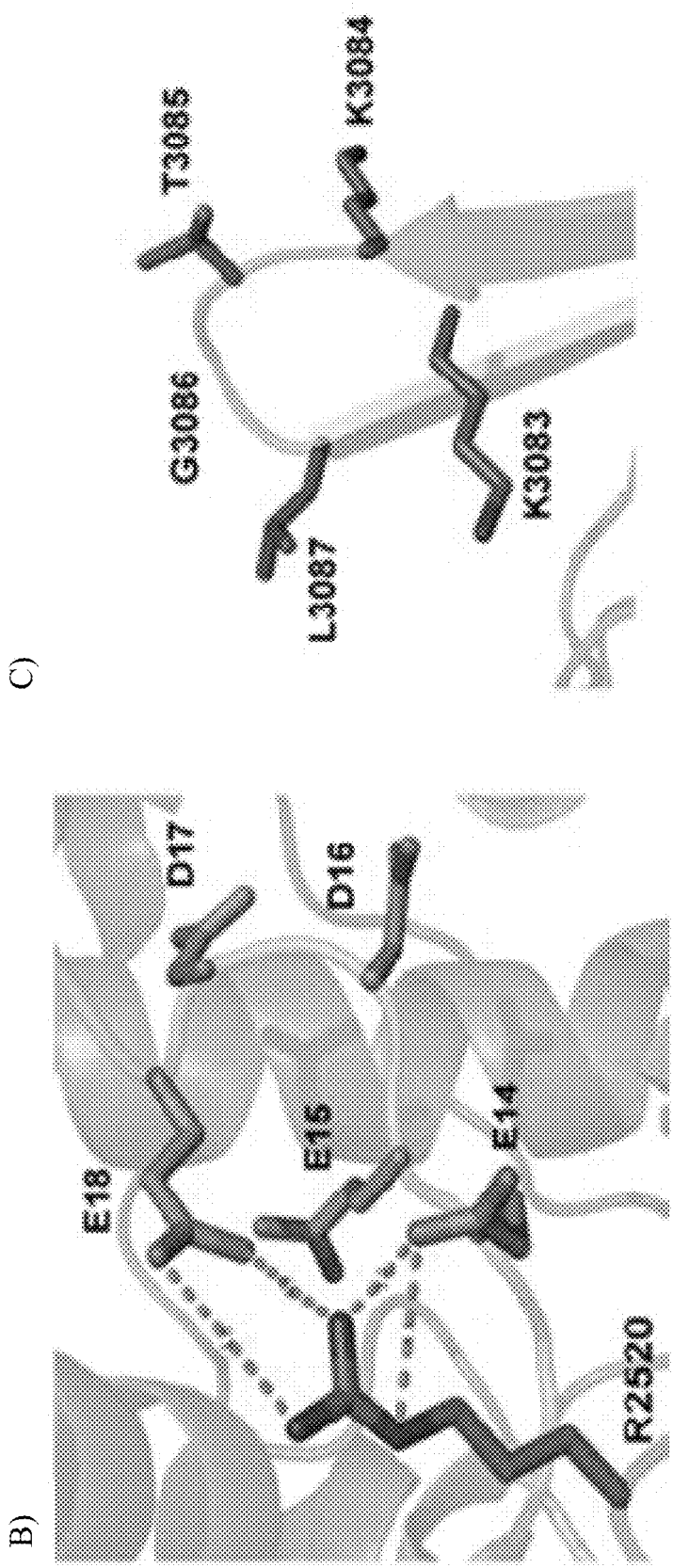

Example 6: Functional Prediction Modeling Reveals Candidate Damaging BRCA2 Mutations We sought to identify somatic mutations that may damage protein function. We used five different algorithms to predict BRCA2 mutations for their destructive effects on the encoded protein, including PolyPhen-2 (Polymorphism Phenotyping v2), SIFT (Sorting Intolerant From Tolerant), PROVEAN (Protein Variation Effect Analyzer), MutPred, and a predictor using support vector machine (SVM) developed by Wei and Dunbrack. We used the consensus result from five predictors. A mutation is predicted to be deleterious if at least three predictors designated it to be deleterious. Structural information was used to verify the predictions. Since there is no human BRCA2 structure containing our mutations available in the Protein Data Bank (PDB), we used a mouse BRCA2 structure PDB: 1MVIU as our template to model human BRCA2. 1IMIU is a complex structure consisting of a mouse BRCA2 chain (sequence 23783115) and human DSS1 proteins (see, FIG. 5, Panel A).

Table 2 shows the consensus result from functional predictors and structural modeling. We further searched for common mutations of BRCA2 in breast and ovarian cancers in the Breast Cancer Information Core (BIC) (world wide web at "research.nhgri.nih.gov/bic/"), and pancreatic and uterine cancer in the COSMIC. Among all missense mutations of BRCA2 in MSI-H CRCs, 9 were previously reported in breast, ovarian, pancreatic and uterine cancers and 14 variants involved the same reported spots in breast cancer but with different amino acid substitutions in CRC. Except for 3, the other 20 mutation hits with history of occurrence in different types of cancer including breast and ovarian have damaging effect on BRCA2 protein (see, Table 2).

Figure 6:
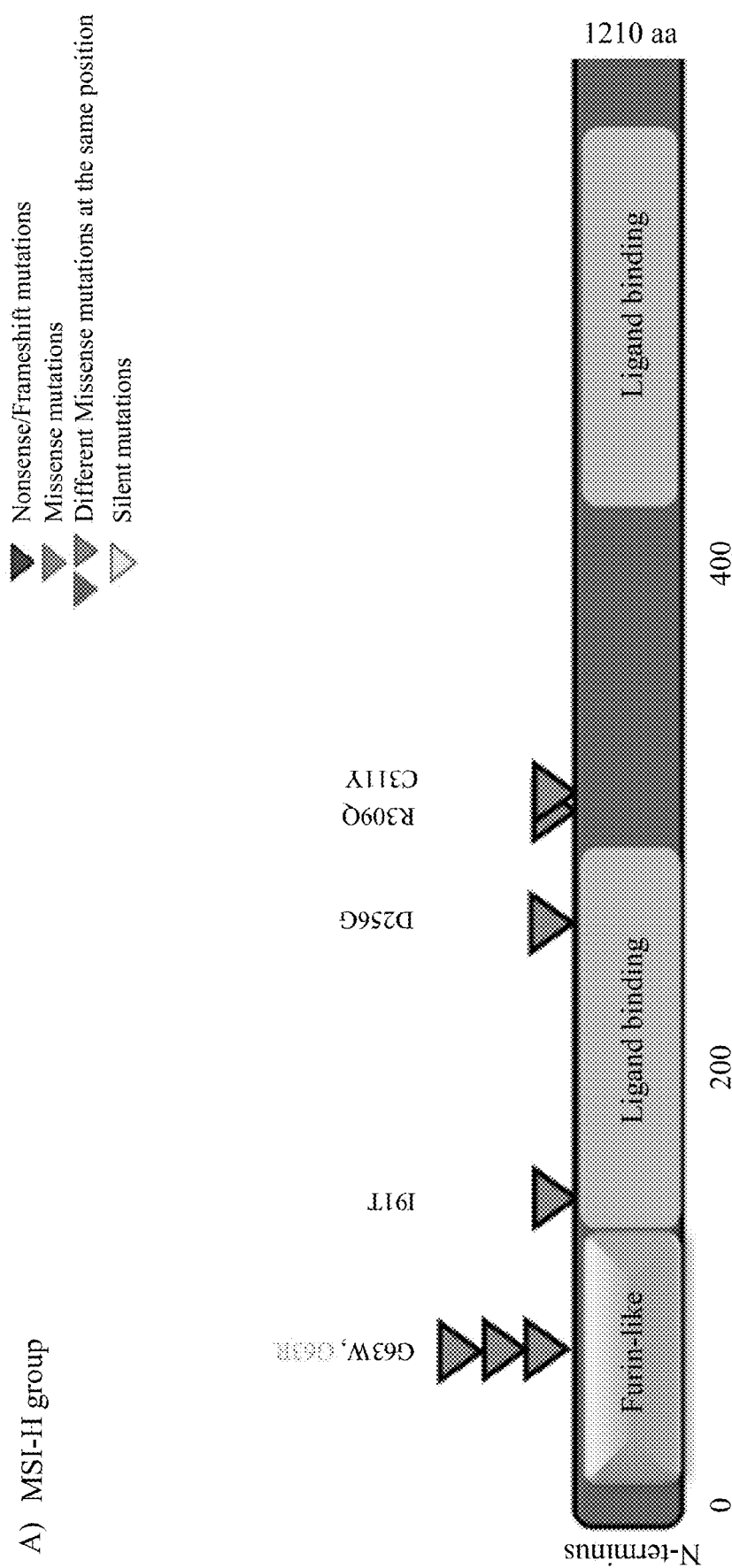
FIG. 6 (Panels A, B, and C): EGFR protein domain structure annotated with activating as well as potentially damaging somatic alterations in MSI-H (Panel A) vs. non-MSI-H (Panel B) CRCs. Functional domains are annotated in different colored-boxes. Truncating variants including nonsense and frameshift mutations are shown in red. Missense mutations are denoted in blue as well as brown in the same spot. Variants predicted by PolyPhen-2 (world wide web at "genetics.bwh.harvard.edu/pph2/") to be damaging are denoted in black-outlined triangle. Orange rectangles outline the mutations with possibility (>50%). Panel C shows a model that depicts mutations in tyrosine kinase domain of EGFR genes. The structure of EGFR kinase domain is showing the WT residues of mutations in orange spheres. The activation loop is colored in magenta and Phenylaniline residue of the DFG motif is shown in green sticks. The known responding mutations to TKI are denoted in red outlined. The figure is generated by PyMOL.
Figure 6:
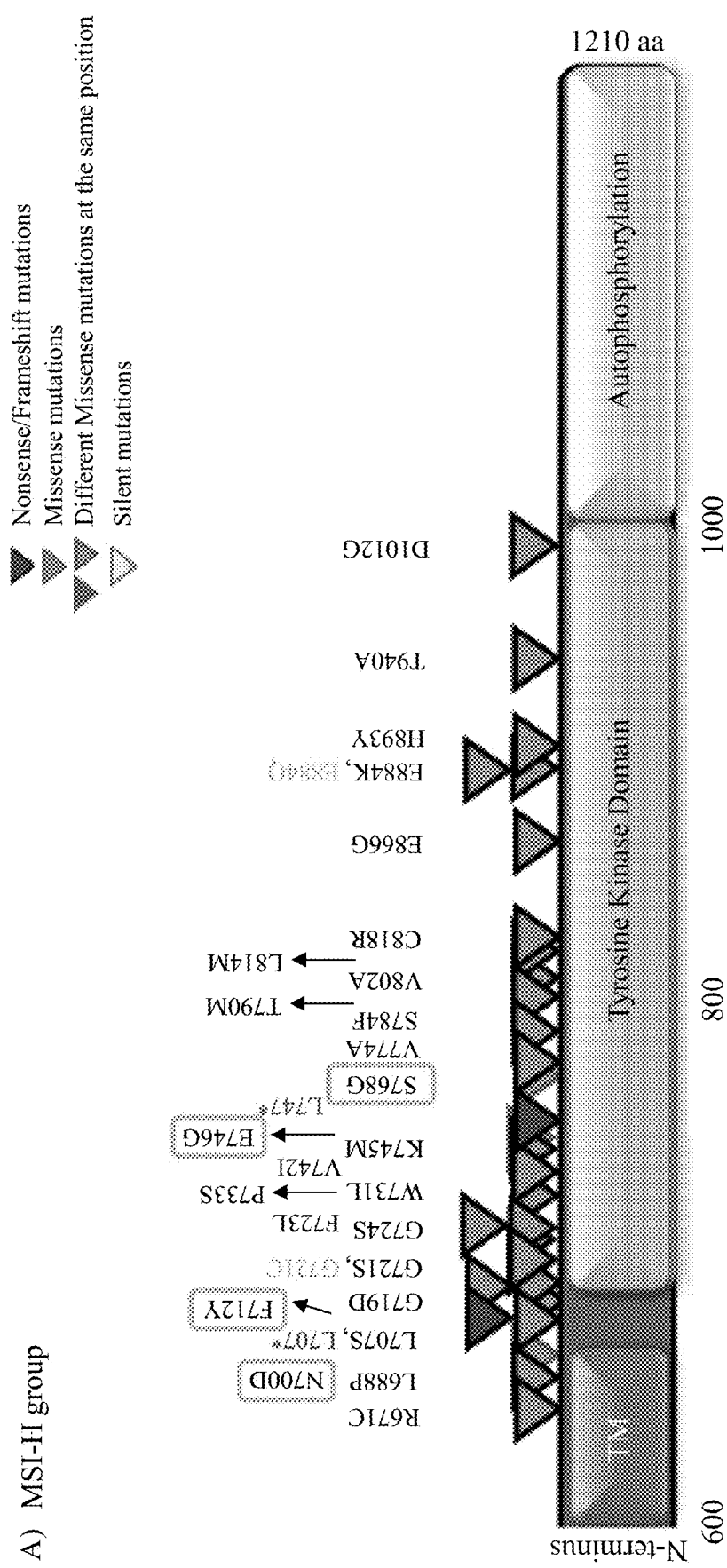
Figure 6:
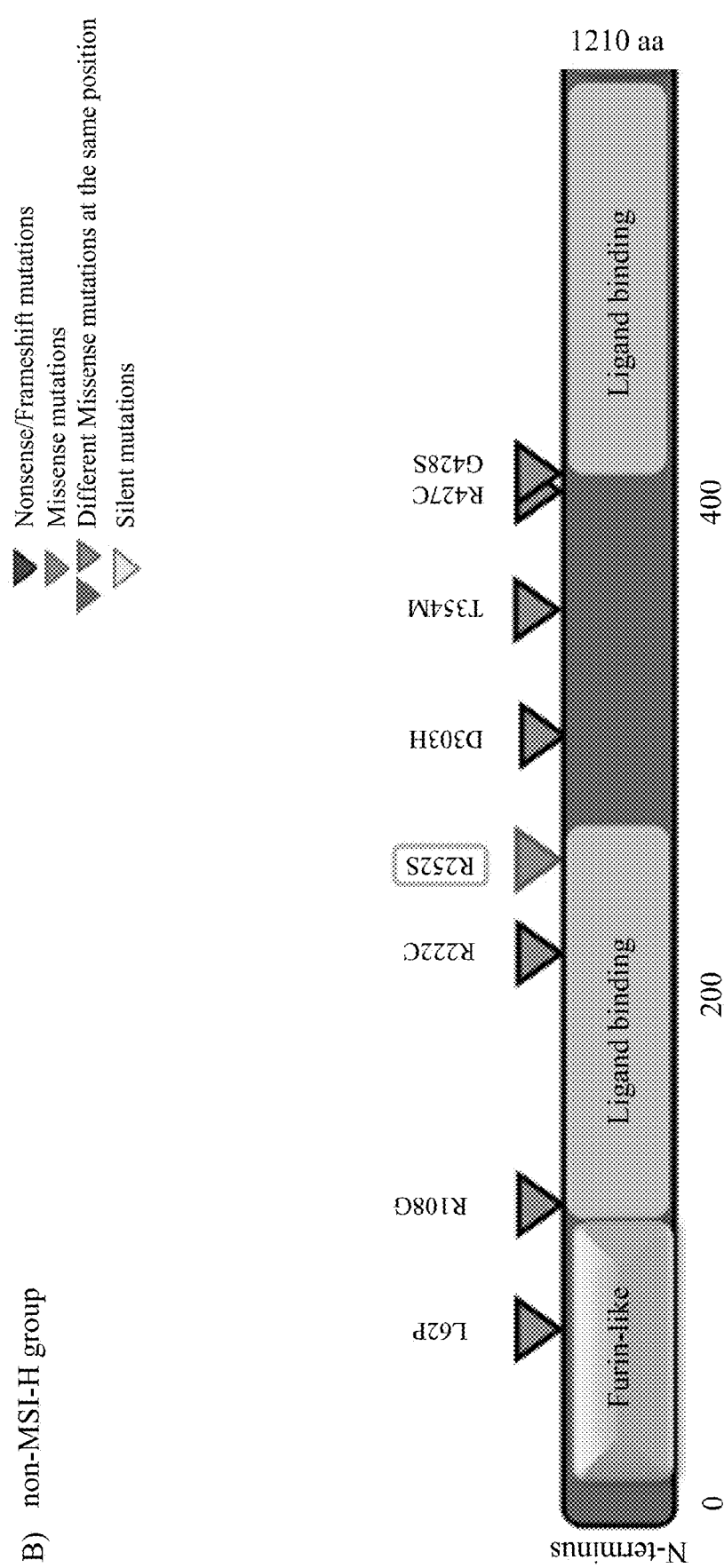
Figure 6:
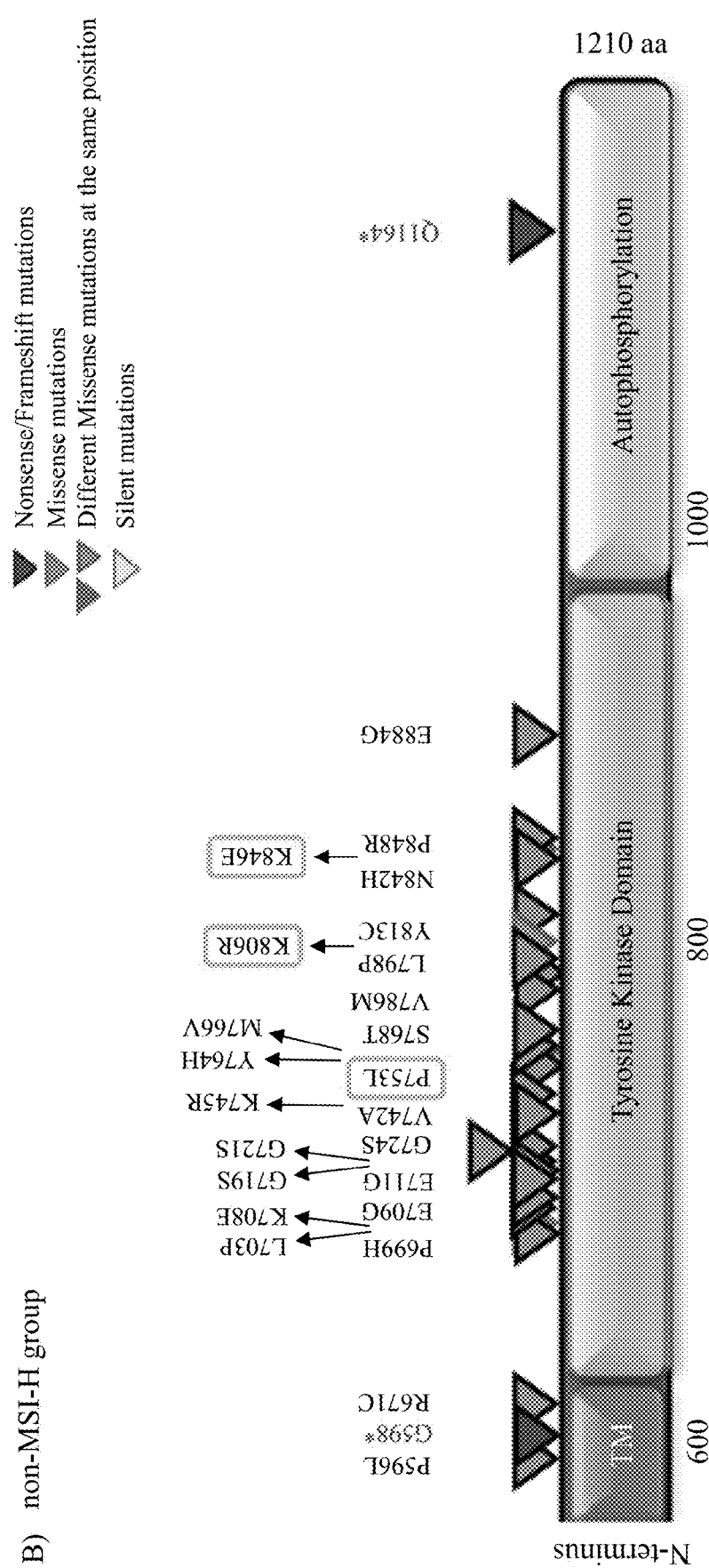
Figure 6:
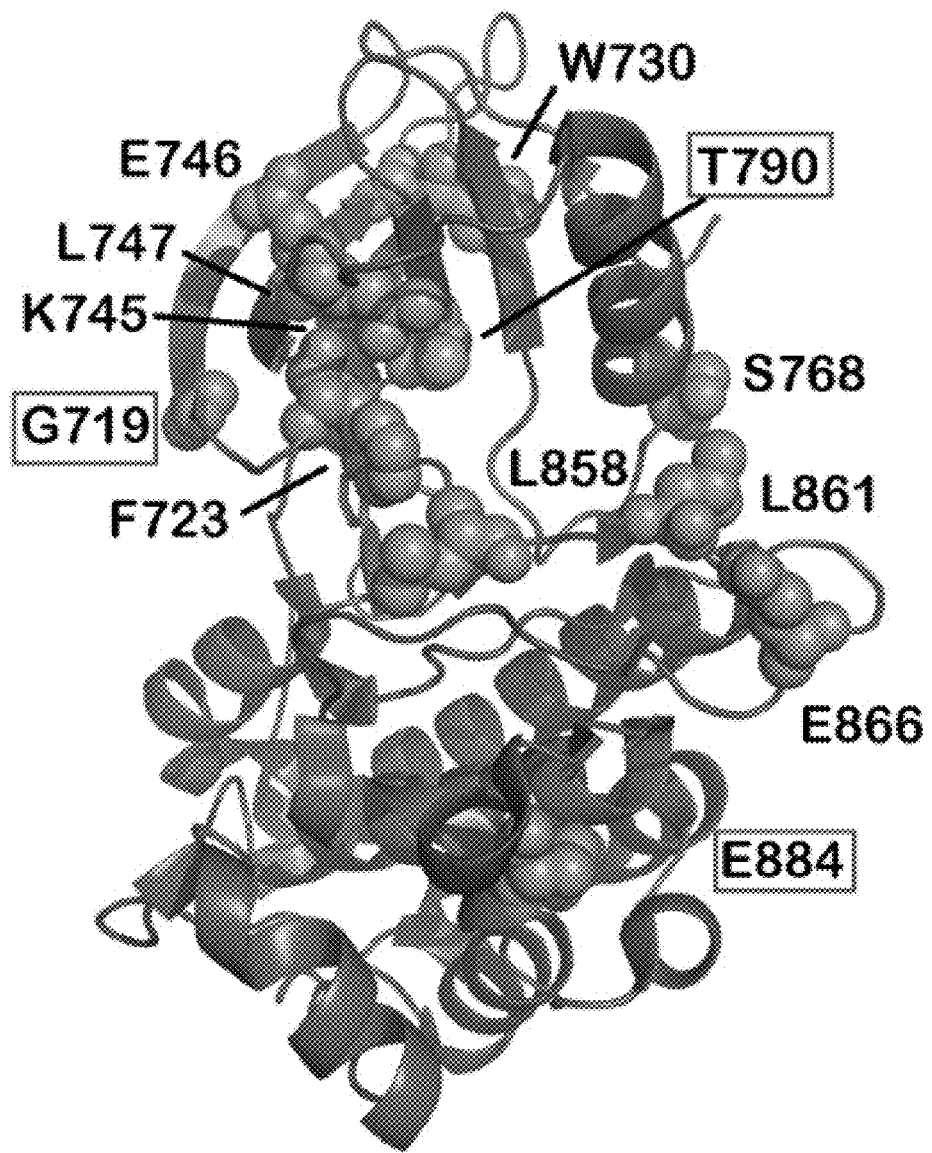
Figure 7:
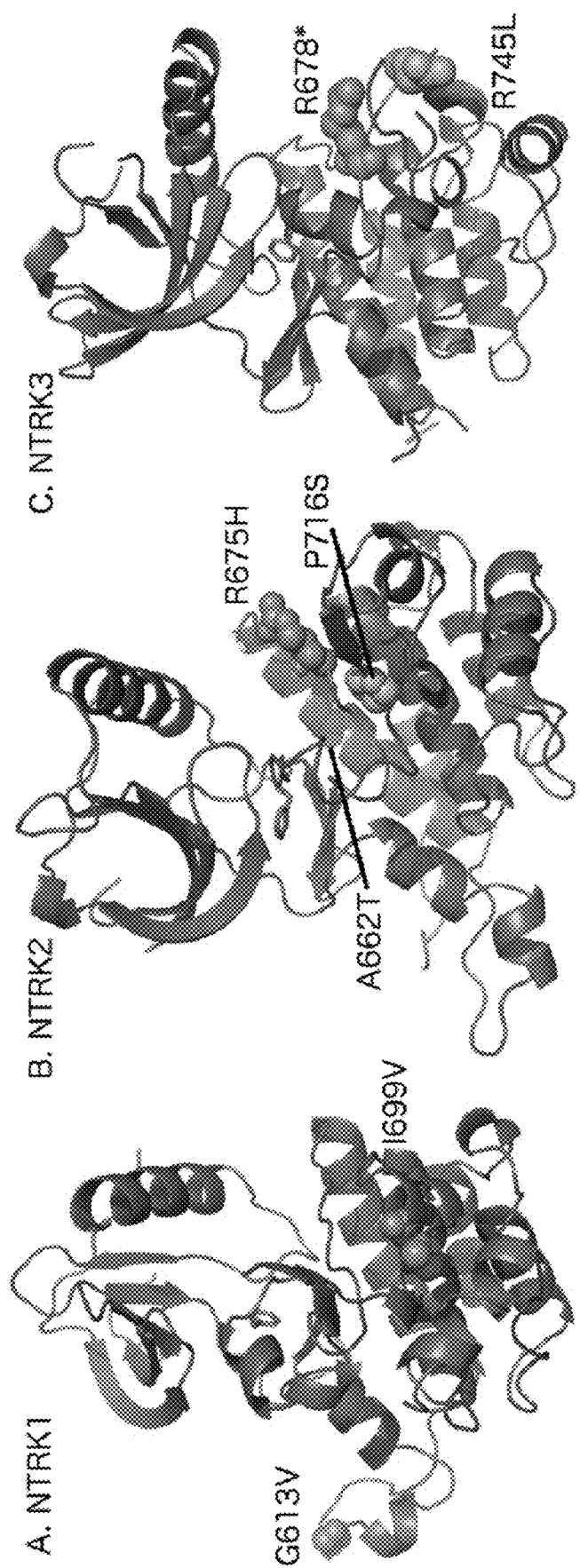
FIG. 7 (Panels A, B and C): (Panel A) The structure of NTRK1 kinase domain showing the WT residues of mutations (I613V, I699V) in orange spheres. The activation loop is colored in magenta and Phenylaniline residue of the DFG motif is shown in green sticks. The figure is generated by PyMOL (https://www.pymol.org/pymol). (Panel B) The structure of NTRK2 kinase domain showing the WT residues of mutations (A662T, R675H, P716S) in orange spheres. (Panel C) The structure of NTRK3 kinase domain showing the WT residues of mutations (R678*, R745L) in orange spheres.

Example 7: EGFR is Highly Mutated in MSI-H CRCs Targeting the Tyrosine Kinase (TK) Domain Unlike the previous reports (Shaib et al., J. Gastrointest. Oncol., 2013, 4, 308-318; and Nagahara et al., Clin. Cancer Res., 2005, 11, 1368-1371), our mutation analysis of the COSMIC dataset revealed a significantly higher EGFR mutation frequency in CRC MSI-H subtype (45.5% vs. 6.5% in non-MSI-H CRCs, p<0.0000001) (see, FIG. 3, Panel B). To determine the domain distribution and functional patterns of EGFR mutations in CRC, we mapped the damaging mutations including nonsense and (deleterious-predicted) missense mutations. Of 101 MSI-H CRCs, 46 patients had 75 EGFR mutations including 2 nonsense (with deleterious effect), 53 missense mutations, and 20 silent mutations (see, Table 1). Somatic EGFR missense mutations derived from the COSMIC database v73 were predicted by PolyPhen-2 and FATHMM for their deleterious/dysfunctional effects, mapped on the EGFR protein structure with respect to known domains (see, FIG. 6). Of 53 missense mutations, 34 (64%) were predicted to be damaging (31 with probability>99% and 4 with probability>50%) (see FIG. 6, Table 1). A high frequency of EGFR mutations (82%) was observed in the TK domain, targeting exons 18-24. Approximately 10-15% of the EGFR mutations found are known activating mutations in the kinase domain and may therefore be actionable through TKI therapy, including the N700D, G719D, T790M, and E884K EGFR mutants. Of note, the most common EGFR mutation (L858R) observed in lung cancer was not found on the MSI-H CRC COSMIC dataset. The observed EGFR L747* in MSI-H CRC involves a hotspot that is frequently involved in lung cancer as various small in-frame deletions leading to kinase activation and sensitivity to TKI therapy. However, in MSI-H CRC as a stop codon the protein is truncated early in the kinase domain and would not lead to kinase activation or EGFR inhibitor sensitivity. EGFR T725M detected in the Caris cohort of MSI-H CRCs is activating in the absence of EGFR ligand (U et al., PLoS Comput. Biol., 2014, 10, e1003545). The observed kinase-activating EGFR mutants retain the extracellular domain with may be used for targeted therapy by antibodies or small molecules targeting the TK domain (see, FIG. 6). EGFR protein expression can be regulated transcriptionally, however, our analysis found no significant difference in EGFR mRNA expression between the MSI-H and non-MSI-H groups (see, FIG. 9).

Example 8: NTRK Gene Mutations Occur in MSH2/MLH1-Mutated CRCs

We searched for mutations in NTRK1/2/3 genes because of the availability of small molecule therapeutic kinase domain inhibitory agents that are currently under investigation in clinical trials. NTRK mutations are rare and we hypothesized they may be enriched in MSI-H CRCs due to increased mutation frequency. Our analysis of TCGA shows that 40% of MSH2/MLH1-mutant CRCs have NTRK mutations versus 16% of non-MSI-H patients (p-value 0.0003). We identified NTRKs mutations in tyrosine kinase domains of NTRK genes including NTRK1 (G613V, I699V), NTRK2 (P716S, R675H, A662T) and NTRK3 (R678*, R745L). These are newly recognized to occur in MSH2/MLH1-mutant (MSI-H predicted) CRCs. G613V (NTRK1) and A662T (NTRK2) are conservative mutations far from the activation loop and also located on the surface of the protein; it is likely that they are neutral mutations. However, R675H (NTRK2) and R678* (NTRK3) are both located at the arginine position of the catalytic HRD motif. Both will inactivate the kinase domain through disrupting the catalytic machinery or producing a truncated protein, respectively. Finally, three of the mutations are either in the activation loop (NTRK2 P716S) or immediately adjacent to it both in sequence and structure (NTRK1 I699V and NTRK3 R745L). They could destabilize the inactive conformation of the kinase domain thereby potentially activating the kinase.

MSI caused by a deficient MMR system leads to the hypermutable phenotype that is detected in about 15% of all CRCs. Each cancer and its subtypes are characterized by a specific somatic mutation signature. Large-scale tumor sequencing studies have produced numerous correlations (Torkamani et al., Cancer Res., 2008, 68, 1675-1682). However, distinguishing tumor "driver" mutations from "passenger" mutations can be a challenge. Functionally damaging mutations or cancer driving mutations are usually differentiated from neutral mutations based on their frequency despite the fact that they could occur at very low frequencies among tumors (Sakoparnig et al., PLoS Comput. Biol., 2015, 11, e1004027).

There is a lack of microsatellite instability status designation in the COSMIC database. Hence, we designed the cohorts based on the presence or absence of common MMR gene mutations associated with the MSI-H phenotype. CRC patients harboring non-synonymous mutations in MMR genes, other than MLH1 and MSH2, were designated as MSI-L. MSI-L samples that are typically associated with a weak MMR-deficiency phenotype were neither included in the non-MSI-H group nor statistically analyzed in our study. Less than 4 percent of non-MSI-H patients in the COSMIC database were noted to have >1000 mutated genes, in which 36% harbored $POL_E$ and EXO1 mutations. These were not excluded from analysis of non-MSI-H tumors because they were not expected to have microsatellite instability.

The BRCA2 protein is a fundamental element of HR and somatic mutations in BRCA2 are known cancer drivers. The high frequency of repetitive sequences in BRCA2 could allow for frequent mutations in MSI tumors. Our data show a distinct pattern and comparatively frequent BRCA2 mutations in MSI-H CRCs. Functionally damaging mutations predicted in BRCA2 may disrupt the protein-protein interactions (see, FIG. 3, Panel A, Table 2). Homologous recombination is defective in cancer cells with mutant BRCA1 or BRCA2 genes, leading to more genetic abnormalities. Our results represent the accumulation of relatively CRC-exclusive BRCA2 mutations in the C-terminal area where BRCA2 interacts with DSS1 and RAD51 to facilitate HR. Yet to be further studied, discriminating the environmental influence on somatic mutations as tumor specific ones may be pursued. Dysfunctional or semi-functional BRCA2 can effect on drug sensitivity, especially if biallelic. Likewise, we show that mutations in the BRCT domains of BRCA2 is another hotspot, contributing to partial functionality or even protease-mediated degradation. It is clear based on present knowledge that tumors with biallelic loss of BRCA2 may be considered for therapeutic strategies that use PARP inhibitors. There is a lack of availability of allele frequency in COSMIC database, particularly for BRCA2 mutations.

EGFR has an extracellular ligand-binding domain, a single membrane-spanning region, and a cytoplasmic tyrosine kinase domain. Activation of the EGFR by a ligand leads to phosphorylation of its cytoplasmic tail. EGFR activation stimulates complex intracellular signaling pathways such as RAS-RAF-MAPK and PTEN-PI3K-AKT pathways. A group (Pao et al., PLoS Med., 2005, 2, e73) previously reported a frequency of 22.4% of EGFR mutations targeting exon 18 in CRC patients in Korea. Our mutational analysis of the COSMIC dataset indicates a 45.5% EGFR mutation frequency in CRC patients with MSI-H tumors.

EGFR mutations detected in CRC mainly target the TK domain, covering exons 18-24, which may be used for therapeutic targeting by anti-EGFR antibodies or small molecule EGFR inhibitors. Although rare nonsense EGFR mutations leading to truncated protein were detected in CRCs, we predicted about 65% of EGFR missense mutations targeting the TK domain are either activating or damaging by applying available predictors (see, FIG. 6, Table 1).

The interaction between proteins and background expression patterns can be utilized in pharmacological studies. We did not detect a different mRNA expression level of EGFR mRNA between CRC subtypes. There is a lack of access to the protein expression level of EGFR in COSMIC database. Furthermore, NSCLCs with EGFR mutations and relatively half of CRC patients without KRAS mutation benefit from anti-EGFR therapies. We detected 477 (43%) colorectal cancer patients profiled in COSMIC V73 to have KRAS mutations, reflecting that almost half of CRC patients are not responsive to anti-EGFR antibody therapies. Non-MSI-HCRCs with KRAS mutations, in particular, were highly (80%) mutated in the G12 and G13 positions such as GT3V and GT3D compared to 14 (26%) MSI CRCs. The data suggests that non-MSI-H patients are more likely to harbor KRAS mutations that make them resistant to anti-EGFR antibodies such as Cetuximab or panitumumab.

The limited response to EGFR therapy may in part be related to BRAF mutations, which are significantly increased in MSI-H CRCs, or possibly due to lack of patient selection, i.e. targeting patients with EGFR mutation as we may suggest here as part of a precision medicine approach. EGFR inhibitors targeting tyrosine kinase (TKI) are not known to be effective drugs for CRC patients with KRAS mutation. Moreover, the T790M mutation in EGFR confers resistance to EGFR TKIs Gefitinib or Erlotinib (see, FIG. 6). The EGFR T790M mutation may rarely occur as a primary resistance mutation together with a sensitizing mutation. Our data is indicative of the presence of a patient with T790M mutation before treatment profiled by the COSMIC. Osimertinib, a third-generation EGFR inhibitor, targets the T790M mutation in EGFR. On the other hand, patients with N700D, and G719D have been reported to be sensitive to TKIs and may benefit from Gefitinib or Erlotinib. While L747 in frame deletion mutants are common in lung cancer and are sensitive to EGFR TKIs, the L747* in MSI-H would not be expected to activate the kinase and is predicted to be insensitive to TKIs. The EGFR E884K mutation confers sensitivity to Gefitinib, but resistance to Erlotinib. EGFR T725M detected in our initial cohort MSI-H CRCs (Caris Life Sciences), is reported in cell-based assays to increase EGFR activity in the absence of EGFR ligand. EGFR activating mutations don't necessarily disrupt the folding or stability of the protein but increase its dynamic and functional prediction of the mutations via bioinformatics tools. These tools are helpful but not sufficient. Characterizing the EGFR activating mutations via identifying autophosphorylation of EGFR via immunohistochemistry (IHC) can be done to establish which CRC patients with EGFR mutated tumors may derive any benefit from EGFR-targeted therapeutics.

Considering the approximate 134,000 new cases of CRC per year in the United States, 13,000-18,000 are expected to be part of an MSI-H cohort and among them, there would be about 6000-9000 patients with EGFR mutations. These patients may benefit from EGFR inhibitors including antibodies such as Cetuximab, Panitumumab or small molecules such as Erlotinib, Gefitinib or Osimertinib. Most of these patients have early stage disease and would not require chemotherapy. However, it is important to further investigate whether selected patients with metastatic disease that is MSI-H (who likely represent a smaller subset of 2000-3000 patients per year) who have no remaining therapeutic options, and who may have progressed on immunotherapy, may derive some benefit from TKI therapy. Based on our results, a subset of the patients with MSI-H advanced disease, perhaps a few hundred patients each year in the US, should have actionable kinase activating EGFR mutations that may respond to the various anti-EGFR therapeutics. This approach can be generalized for other oncogenic driver RTKs activated more in MSI-H patients. For example, our analysis of TCGA has shown 40% of MSI-H patients have NTRK mutations in comparison to 16% of non-MSI-H patients (p value 0.0003). Among these NTRK mutations in TCGA, NTRK1 (G613V, I699V), NTRK2 (P716S, R675H, A662T) and NTRK3 (R678*, R745L) are newly recognized to occur in MSI-H CRCs and the mutations within the kinase domain with potential to activate and serve as drivers in MMR-deficient tumors. There are potent kinase inhibitors against NTRK mutated cancers currently being tested in clinical trials.

Overall, we characterized BRCA2, EGFR, and NTRK mutations in CRC patients, focusing on the mutations that offer insight into pathogenesis and have significant clinical therapy implications. Our results showing frequent BRCA2, EGFR, and NTRK mutations in MSI-H CRC patients offer immediate novel personalized medicine strategies to treat the patients with advanced disease who may have no remaining treatment options.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety. The subject matter described herein was made with government support under Grant No. P30 CA006927 awarded by the National Institutes of Health (NIH).

What is claimed is:

1. A method for diagnosing and treating colorectal cancer having high microsatellite instability in a subject in need thereof, comprising:
   analyzing a sample from the subject for the presence of one or more mutations in EGFR selected from the group consisting of N700D, G719D, T725M, T790M, or E884K and/or NTRK1 which is I699V, and/or NTRK2 which is P716S, and/or NTRK3 which is R745L, wherein the subject is diagnosed with colorectal cancer having high microsatellite instability if the one or more mutations in EGFR and/or NTRK are detected; and
   administering a therapeutic agent to the diagnosed subject, wherein the therapeutic agent is an agent used to treat EGFR-related cancer and/or NTRK-related cancer.

2. The method according to claim 1, wherein the therapeutic agent is a chemotherapeutic agent.

3. The method according to claim 2, wherein the chemotherapeutic agent is a tyrosine kinase inhibitor.

4. The method according to claim 1, wherein the therapeutic agent is Cetuximab, Panitumumab, Erlotinib, Gefitinib or Osimertinib.

5. A method for treating colorectal cancer having high microsatellite instability in a subject in need thereof, comprising:
   requesting a test providing the results of an analysis of a sample from the subject for the presence of one or more mutations in EGFR and/or NTRK, wherein the subject is diagnosed with colorectal cancer having high microsatellite instability if the one or more mutations in EGFR and/or NTRK are detected, wherein the mutation in EGFR is N700D, G719D, T725M, T790M, or E884K, and the mutation in NTRK is I699V in NTRK1, P716S in NTRK2, or R745L in NTRK3; and
   administering a therapeutic agent to the diagnosed subject, wherein the therapeutic agent is an agent used to treat EGFR-related cancer or NTRK-related cancer.

6. The method according to claim 5, wherein the sample is a biopsy from the subject.

7. The method according to claim 5, wherein the therapeutic agent is a chemotherapeutic agent.

8. The method according to claim 7, wherein the chemotherapeutic agent is a tyrosine kinase inhibitor.

9. The method according to claim 5, wherein the therapeutic agent is Cetuximab, Panitumumab, Erlotinib, Gefitinib or Osimertinib.

10. A method for treating colorectal cancer having high microsatellite instability in a subject in need thereof, comprising:
    analyzing a sample from the subject for the presence of one or more mutations in EGFR and/or NTRK, wherein the mutation in EGFR is N700D, G719D, T725M, T790M, or E884K, and the mutation in NTRK is I699V in NTRK1, P716S in NTRK2, or R745L in NTRK3, wherein the colorectal cancer has high microsatellite instability if one or more mutations in EGFR and/or NTRK is detected; and administering a therapeutic agent to the subject having one or more mutations in EGFR and/or NTRK, wherein the therapeutic agent is an agent used to treat EGFR-related cancer or NTRK-related cancer.

11. The method according to claim 10, wherein the sample is a biopsy from the subject.

12. The method according to claim 10, wherein the therapeutic agent is a chemotherapeutic agent.

13. The method according to claim 10, wherein the chemotherapeutic agent is a tyrosine kinase inhibitor.

14. The method according to claim 10, wherein the therapeutic agent is Cetuximab, Panitumumab, Erlotinib, Gefitinib or Osimertinib.

* * * * *